US007101976B1

(12) United States Patent
Kilpatrick et al.

(10) Patent No.: US 7,101,976 B1
(45) Date of Patent: Sep. 5, 2006

(54) EPHA2 MONOCLONAL ANTIBODIES AND METHODS OF MAKING AND USING SAME

(75) Inventors: Katherine E Kilpatrick, Durham, NC (US); Michael Scott Kinch, Laytonsville, MD (US); Kelly Carles-Kinch, Laytonsville, MD (US)

(73) Assignees: Purdue Research Foundation, West Lafayette, IN (US); SmithKline Beecham Corporation, Philadelphia, PA (US)

( * ) Notice: Subject to any disclaimer, the term of this patent is extended or adjusted under 35 U.S.C. 154(b) by 326 days.

(21) Appl. No.: 09/952,560

(22) Filed: Sep. 12, 2001

Related U.S. Application Data

(60) Provisional application No. 60/232,302, filed on Sep. 12, 2000, now abandoned.

(51) Int. Cl.
C07K 16/00 (2006.01)
C12P 21/08 (2006.01)

(52) U.S. Cl. .................. 530/387.1; 530/357.3; 530/387.7; 530/388.1; 530/388.5; 530/358.5; 530/389.1; 530/388.7

(58) Field of Classification Search .............. 424/130.1; 530/387, 387.1, 387.3, 388.1, 387.7, 388.15, 530/388.8, 389.1, 389.7
See application file for complete search history.

(56) References Cited

U.S. PATENT DOCUMENTS

| 5,824,303 A | 10/1998 | Bartley et al. |
| 2001/0031252 A1 | 10/2001 | Low et al. |

FOREIGN PATENT DOCUMENTS

| WO | WO 93/00425 | 1/1993 |
| WO | WO 94/29348 | 12/1994 |
| WO | WO 98/43960 | 10/1998 |
| WO | WO 00/30673 | 6/2000 |
| WO | WO 01/12840 A3 | 2/2001 |

OTHER PUBLICATIONS

Asaheim et al. "A splice variant of human ephrin–A4 encodes a soluble molecule that is secreted by activated human B lymphocytes." *Blood*. 2000;95(1):221–30.
Andres et al., "Expression of two novel *eph*–related receptor protein tyrosine kinases in mammary gland development and carcinogenesis," *Oncogene*, 1994; 9:1463–1467.
Baggliolini et al. "Interleukin–8 and the Chemokine Family" *Int. J. Immunopharmae* 1995;17(2):103–108.
Biervert et al. "Semiquantitative expression analysis of ephrine–receptor tyrosine kinase mRNA's in a rat model of traumatic brain injury." *Neurosci Lett.* 2001;315(1–2):25–8.
Blanco et al. "Expression of EphA receptors and ligands during chick cerebellar development." *Mech Dev.* 2002;114(1–2):225–9.

Bodansky et al., Ed., *Principles of Peptide Synthesis*, Springer–Verlag Inc., NY, 1993, Cover pg., Publication pg., and Table of Contents.
Boerner et al."Production of antigen–Specific Human Monoclonal Antibodies from in vitro–primed Human Splenocytes", *J. Immunol.*, 1991; 147(1):86–95.
Bohme et al. "PCR mediated detection of a new human receptor–tyrosine–kinase, HEK 2." *Oncogene*. 1993;8(10):2857–62.
Bovenkamp et al. "egenerate PCR–based cloning method for Eph receptors and analysis of their expression in the developing murine central nervous system and vasculature" *DNA Cell Biol.* 2001:20(4):203–13.
Brady–Kalnay et al., "Dynamic Interaction of PTPµ with Multiple Cadherins In Vivo" *J. Cell Biol.*, 1998; 141:287–296.
Brantley et al. "Soluble Eph A receptors inhibit tumor angiogenesis and progression in vivo." *Oncogene*. 2002;21(46):7011–26.
Bruggemann et al., "Designer mice: the production of human antibody repertoires in transgenic animals" *Year Immunol.* 1993;7:33–40.
Burgess et al. "Possible Dissociation of the Heparin–binding Mitogenic Activities of Heparin–binding (Acidic Fibroblast) Growth Factor–1 from Its Receptor–binding Activities by Site–directed Mutgensis of a Single Lysine Residue" *J. Cell Biology* 1990;111:2129–2138.
Carles–Kinch "Antibody Targeting of the EphA2 Tyrosine Kinase Inhibits Malignant Cell Behavior," *Cancer Research* 2002;62:2840–2847.
Carter et al. "EphrinA1–induced cytoskeletal re–organization requires FAK and p130(cas)." *Nat Cell Biol.* 2002;4(8):565–73.
Chen et al. "An enhancer element in the EphA2 (Eck) gene sufficient for rhombomere–specific expression is activated by HOXA1 and HOXB1 homeobox proteins." *J Biol Chem.* 1998;273(38):24670–5.

(Continued)

*Primary Examiner*—Susan Ungar
(74) *Attorney, Agent, or Firm*—Needle & Rosenberg, P.C.

(57) ABSTRACT

The invention provides a monoclonal antibody, a fragment thereof, or a molecular complex thereof that binds to an extracellular domain of an EphA2 receptor molecule, wherein binding of the monoclonal antibody or fragment thereof to the EphA2 receptor molecule present in the membrane of a cancer cell favorably alters activity of the EphA2 receptor molecule. The invention further relates to methods of making and using the monoclonal antibodies, fragments, and molecular complexes regarding the same. The monoclonal antibodies of the present invention target the extracellular domain of EphA2 and operate to redirect the function of EphA2 to selectively block the growth and invasiveness of metastatic cells. The invention thus makes possible therapeutic strategies that optimally target metastatic cells while preventing collateral damage to normal tissues.

21 Claims, 1 Drawing Sheet

OTHER PUBLICATIONS

Chen et al. "Germ–line inactivation of the murine Eck receptor tyrosine kinase by gene trap tetroviral insertion." *Oncogene* 1996;12(5):979–88.

Chen et al., "Integrin–mediated cell adhesion activates mitogen–activated protein kinases," *J. Biol. Chem.*, 1994;269:26002–26005.

Cheng et al. "Blockade of EphA Receptor Tyrosine Kinase Activation Inhibits Vascular Endothelial Cell Growth Factor–Induced Angiogenesis." *Mol Cancer Res.* 2002;1(1):2–11.

Clark et al. "Aberrant function of the Ras signal transduction pathway in human breast cancer" *Breast Cancer Res. Treat.*1995;35(1):133–144.

Clark et al. "The Ras–related protein Fheb is farnesylated and antagonizes Ras signaling and transformation," *J. Biol. Chem.*, 1997; 272:10608–10615.

Cole et al., Monoclonal Antibodies and Cancer Therapy, Alan R. Liss, 1985, p. 77.

Connor et al. "Expression and tyrosine phosphorylation of Eph receptors suggest multiple mechanisms in patterning of the visual system." *Dev Biol.* 1998;193(1):21–35.

Curti "Physical barriers to drug delivery in tumors" Critical Reviews in Oncology/Hematology1993;14:29–39.

D'Amico "Predicting the Sites of Metastasis Form Lung Cancer Using Molecular Biologic Markets" *Ann. Thoracic. Surg.* 2001;72:1144–8.

Dawson et al., "Synthesis of Proteins by Native Chemical Ligation," *Science*, 1994;266:776–779.

Dermer "Another Anniversary for the War on Cancer" Bio/Technology 1994;12:320.

deLisle et al., *Techniques in Protein Chemistry IV*, Academic Press, New York, 1992, pp. 257–267.

DeVita, Jr., "Principles of Cancer Management: Chemotherapy", *Cancer: Principles and Practice of Oncology, Fifth Edition*, V. T. Devita Jr. et al., Eds., Lippincott–Raven, Philadelphia, 1997;333–347.

Dohn et al. "Receptor tyrosine kinase EphA2 is regulated by p53–family proteins and induces apoptosis." *Oncogene.* 2001;20(45):6503–15.

Easty et al., "Novel and Known Protein Tyrosine Kinases and Their Abnormal Expression in Human Melanoma," *J. of Investigative Dermatolog*, 1993;101:679–684.

Eatsy et al., "Protein tyrosine kinases in malignant melanoma," *Melanoma Research*, 2000;10:401–411.

Easty et al. "Up–regulation of ephrin–A1 during melanoma progression." *Int J Cancer.* 1999;84(5):494–501.

Fenrick "TEL, a Putative Tumor Suppressor, Modulates Cell Growth and Cell Morphology of Ras–Transformed Cells While Repressing the Transcription of *stromelysin–1*" Molecular and Cellular Biology 2000;20(6):5826–5839.

Ferrone et al., eds., *Handbook of Monoclonal Antibodies*, Noges Publications, Park Ridge, N.J., 1985. Chapter 22 and 303–357.

Fidler, "Molecular Biology of Cancer: Invasion and Metastasis", *In Cancer: Principles and Practice of Oncology*, V. T. Devita et al, eds. (Philadelphia: Lippincott–Raven), p. 135–152 (1997).

Freshney *Culture of Animal Cells. A Manual of Basic Technique 1983;3–4.*

Frisch, "Integrins and anoikis", *Current Opinion in Cell Biology*, 1997;9:701–706.

Ganju et al. "The Eck receptor tyrosine kinase is implicated in pattern formation during gastrulation, hindbrain segmentation and limb development." *Oncogene.* 1994;9(6):1613–24.

Grant, *Synthetic Peptides: A User Guide*, W.H. Freeman and Co., N.Y., 1992, Cover pg., Publication pg., and Table of Contents only.

Goding, *Monoclonal Antibodies: Priciples and Practice, Academic Press*, 1986, pp. 59–103.

Harlow et al., *Antibodies, A Laboratory Manual*, Cold Spring Harbor Publications, New York, 1988. Table of Contents Only.

Hartwell et al. "Integrating Genetic Appraoches into the Discovery of Anticancer Drugs" *Science* 1997;278:1064–1068.

Hein, "Regulation of Cell Signaling Induced by the Cell Adhesion Molecule, E–Cadherin," Ph.D. Thesis, Purdue University, 94 pgs., Cover Date Aug. 1999.

Helbling et al. "Requirement for EphA receptor signaling in the segregation of Xenopus third and fourth arch neural crest cells." *Mech Dev.* 1998;78(1–2):63–79.

Henson, "Molecular and genetic targets in early detection", *Current Opinion in Oncology*,1999;11:419–425.

Hess et al., "Molecular regulation of tumor cell vasculogenic mimicry by tyrosine phosphorylation: Role of epithelial cell kinase (ECK/EphA2)," *Cancer Res.*, 2001; 61:3250–3255.

Hoogenboom et al.,:By–passing Immunisation Human Antibodies from Synthetic Repertoires of Germline $V_H$ Gene Segments Rearranged *in Vitro J. Mol. Biol.*, 1991;227:381–388.

Hunter et al. "Novel receptor protein–tyrosine kinases" *Adv Second Messenger Phosphoprotein Res.*1990;24:260–5.

Hunter et al. "Receptor protein tyrosine kinases and phosphatases." Cold Spring Harb Symp Quant Biol. 1992;57:25–41.

Jain "Barriers to Drug Delivery in Solid Tumors" *Scientific American*, 1994;58–65.

Jakobovits et al., "Analysis of homozygous mutant chemeric mice: Delection of the immunoglobulin heav–chain joining region blocks B–cell development and antibody production" *Proc. Natl. Acad. Sci. USA*, 1993; 90:2551–2555.

Jakobovits et al., "Germ–like transmission and expression of a human–derived yeast artificial chromosome" *Nature*, 1993;362:255–258.

Kabat et al., "Sequences of Proteins of Immunological Interest," *National Institutes of Health*, Bethesda, Md. 1987.

Karam et al. "EphA4 is not required for Purkinje cell compartmentation." *Brain Res Dev Brain Res.* 2002;135(1–2):29–38.

Khan et al. Immunohistochemical Localization of Epidermal and Mallory Body Cytokeratin in Undifferentiated Ephithelial Tumors *American Journal of Clinical Pathology* 1984;84:184–191.

Khosravi–Far et al. "Activation of Rac1, RhoA, and Mitogen–Activated Protein Kinases Is Required for Ras Transformation" *Molecular and Cellular Biology* 1995;15(11)6443–6453.

Kikawa et al. "Regulation of the EphA2 kinase by the low molecular weight tyrosine phosphatase induces transformation." *J Biol Chem.* 2002;277(42):39274–9.

Kinch et al., "Cell adhesion mediated by CD4 and MHC class II proteins requires active cellular processes," *J. Immunol.*, 1993; 151:4552–4561.

Kinch et al., "Cytometric analysis of cell contact and adhesion," *Cytometry*, Darzynkiewicz et al., Eds., 3$^{rd}$ Ed. Academic Press, San Diego, CA, 2000.

Kinch et al., "Identification of Tyrosine Phosphorylated Adhesion Proteins in Human Cancer Cells," *Hybridoma*, 1998;17:227–235.

Kinch et al. "Overexpression and functional alterations of the EphA2 tyrosine kinase in cancer" *Clinical & Experimental Metastasis* 2003:20:59–68.

Kinch et al "Predictive Value of the EphA2 Receptor Tyrosine Kinase in Lung Cancer Recurrence and Survival" *Clin Cancer Res*. 2003;9(2):613–8.

Kinch et al., "The protein tyrosine kinase p56*lck* regulates cell adhesion mediated by CD4 and MHC class II proteins," *J. Exp Med.*, 1994; 180:1729–1739.

Kirk et al., "The human anti–porcine cell mediated response: In vitro studies of function and molecular interaction," *Transplant*, 1993; 55(4):924–931.

Kohler et al. "Continuous culture of fused cels secreting antibody of predefined specificity" *Nature* 1975;256:495–497.

Koolpe et al. "An ephrin mimetic peptide that selectively targets the EphA2 receptor." *J Biol Chem*. 2002;277(49):46974–9.

Kratchmarova et al. "Characterization of promoter region and genomic structure of the murine and human genes encoding Src like adapter protein." *Gene*. 2001;262(1–2):267–73.

Lai et al. "Expression of Eph receptors in skeletal muscle and their localization at the neuromuscular junction." *Mol Cell Neurosci*. 2001;17(6):1034–47.

Lawrence et al., "Mechanisms of tumor invasion and metastasis", *World J. Urol.*, 1996;14:124–130.

Lazar et al. "Transforming Growth Factor : Mutation of Aspartic Acid 47 and Leucine 48 Results in Different Biological Activities" *Molecular and Cellular Biology* 1998;8(3):1247–1252.

Lickliter et al. "Embryonic stem cells express multiple Eph–subfamily receptor tyrosine kinases." *Proc Natl Acad Sci U S A*. 1996;93(1):145–50.

Marks et al. "By–pasing immunization. Human antibodies from V–gene libraries displayed on phage." *J Mol Biol*. 1991;222(3):581–97.

McLaughlin "Functional consequences of coincident expression of EphA receptors and ephrin–A ligands." *Neuron*. 1999;22(4):636–9.

Miao et al., "Activation of EphA2 kinase suppresses integrin function and causes focal–adhesion–kinase dephosphorylation," *Nat. Cell Biol.*, 2000;2(2):62–69.

Michael et al. "Efficient gene–specific expression of cre recombinase in the mouse embryo by targeted insertion of a novel IRES–Cre cassette into endogenous loci." *Mech Dev*. 1999;85(1–2):35–47.

Miller et al., "The engagement of $\beta_1$ integrins on promonocytic cells promotes phosphorylation of Syk and formation of a protein complex containing Lyn and $\beta_1$ integrin," *Eur. J. Immuno.*, 1999;29:1426–1434.

Miyazaki et al. "EphA2 overexpression correlates with poor prognosis in esophageal squamous cell carcinoma." *Int. J. Cancer*. 2003; 103(5):657–63.

Nakamoto et al. "Diverse roles for the Eph family of receptor tyrosine kinases in carcinogenesis." *Microsc Res Tech*. 2002;59(1):58–67.

Naruse–Nakajima et al. "Involvement of EphA2 in the formation of the tail notochord via interaction with ephrinA1." Mech Dev. 2001;102(1–2):95–105.

New England Biolabs Product Catalog, 1996, p. 164.

Nemoto et al., "Overexpression of Protein Tyrosine Kinases in Human Esphageal Cancer," *Pathobiology*, 1997;65:195–203.

Nishida et al. "Domain–specific olivocereballar projection regulated by the EphA–ephrin–A interaction" *Development*. 2002;129(24):5647–58.

Nowakowski et al. "Structures of the Cancer–Related Aurora–A, FAK, and EphA2 Protein Kinases from Nano-volume Crystallography." *Structure* 2002;10(12):1659–67.

O'Brien et al., "A mechanism for trabecular meshwork cell retraction: Ethacrynic acid initiates the dephosphorylation of focal adhesion proteins," *Exp. Eye Res.*, 1997;65:471–483.

Ogawa et al. "The ephrin–A1 ligand and its receptor, EphA2, are expresed during tumor neovascularization." *Oncogene*. 2000;19(52):6043–52.

Orsulic et al. "Expression of Eph receptors and ephrins is differentially regulated by E–cadherin." *J Cel Sci*. 2000;113(Pt 10):1793–802.

Oslo et al., *Remington's Pharmaceutical Science*, 16$^{th}$ ed., Mack Publ. Co, 1980.

Potla et al. "Reduced expression of EphrinA1 (EFNA1) inhibits three–dimensional growth of HT29 colon carcinoma cells." *Cancer Lett*. 2002;175(2):187–95.

Pratt et al. "Activation of the EphA2 tyrosine kinase stimulates the MAP/ERK kinase signaling cascade" *Oncogene*. 2002;21(50):7690–9.

Rosenberg, "Principles of Cancer Management: Surgical Oncology", *Cancer: Principles and Practice of Oncology, Fifth Edition*, V. T. Devita, Jr. et al., Eds., Lippincott–Raven, Philadelphia, 1997:cover page, table of contents and 295–333.

Ruiz et al. "The expression of the receptor–protein tyrosine kinase gene, eck, is highly restricted during early mouse development." *Mech Dev*. 1994;46(2):87–100.

Ruoslahti, "Fibronectin and Its Integrin Receptors in Cancer" *Advances in Cancer Research*, 1999;76:1–20.

Sliwkowski et al., "Nonclinical Studies Addressing the Mechanism of Action of Trastuzumab (Herceptin)" *Seminars in Oncology*, 1999; 26:60–70.

Stearns et al., "Human xenograft models for prostate cancer," The Prostate, 1998; 36:56–58.

Stein et al. "Eph receptors discriminate specific ligand oligomers to determine alternative signaling complexes, attachment, and assembly responses" *Genes & Development* 1997;667–678.

Stein et al., "Nck recruitment to Eph receptor, EphB1/ELK couples ligand activation to c–Jun kinase," *J. Biol. Chem.*, 1998; 273:1303–1308.

Studer et al. "Genetic interactions between Hoxa1 and Hoxb1 reveal new roles in regulation of early hindbrain patterning." *Development*. 1998;125(6):1025–36.

Straume et al. "Importance of vascular phenotype by basic fibroblast growth factor, and influence of the angiogenic factors basic fibroblast growth factor/fibroblast growth factor receptor–1 and ephrin–A1EphA2 on melanoma progression." *Am J Pathol*. 2002;160(3):1009–19.

Sulman et al. "ECK, a human EPH–related gene, maps to 1p36.1, a common region of alteration in human cancers." *Genomics* 1997;40(2):371–4.

Vignali et al., "Interactions of CD4 with MHC class II molecules, T cell receptors and p56lck," Phil. Trans. Royal Soc. London, 1993; 342:13–24.

Walker–Daniels et al. "C–Cbl–Dependent EphA2 Protein Degradation Is Induced by Ligand Binding" *Mol Cancer Res.* 2002 1(1):79–87.

Walker–Daniels et al., "The Mechanism of EphA2 Protein Degradation: Implications of Increased EphA2 Protein Levels in Metastatic Cancer Cells," *Proceedings of the American Association for Cancer Research Annual Meeting*, 2001;42:840.

Weaver et al., "The development of a funcionally relevant cell culture model of progressive human breast cancer," *Semin. Cancer Biol.*, 1995;6:175–184.

Wendling et al. "Retinoid signaling is essential for patterning the endoderm of the third and fourth pharyngeal arches." *Development.* 2000;127(8):1553–62.

Zantek et al., "Chapter 25: Analysis of Cell Migration," *Methods in Cell Biology*, vol. 63, *Cytometry, Third Edition, Part A*, Darzynkiewicz et al., eds., Academic Press, San Diego, CA, 2001; title page, publication page, and pgs. 549–559.

Zantek et al., "Identification of an adhesion–associated tyrosine kinase that is tightly regulated in breast cancer," *Mol. Bio. Cell, 8*(Supp):134A, abstract 777 (1997); 37th Annual Meeting of the American Society for Cell Biology, (Dec. 13–17, 1997).

Zantek et al. "MCF–10A–NeoST: A New Cell System for Studying Cell–ECM and Cell–Cell Interactions in Breast Cancer" *Clinical Cancer Research* 2001;7:3640–3648.

Zelinski et al. "Estrogen and Myc Negatively Regulate Expression of the EphA2 Tyrosine Kinase" *Journal of Cellular Biology* 2002;85:714–720.

Zhong et al., "Rho–stimulated contractility contributes to the fibroblastic phenotype of ras–transformed epithelial cells," *Mol Biol Cell*, 1997; 8:2329–2344.

SEQUENCE LISTING

```
<160> NUMBER OF SEQ ID NOS: 2

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 1

Tyr Thr Leu Phe Ser His Ala Val Ser Ser Asn Gly Asn
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 2

Ser Gly Ala Thr Asn Ser Leu His Asn Phe Ser Val Tyr
1               5                   10
```

EPHA2 MONOCLONAL ANTIBODIES AND METHODS OF MAKING AND USING SAME

CROSS REFERENCE TO RELATED APPLICATIONS

This application claims the benefit of U.S. Provisional Application Ser. No. 60/232,302, filed Sep. 12, 2000, now abandoned the entirety of which is incorporated herein by this reference.

BACKGROUND

Metastasis is the leading cause of cancer death. Once cancer has spread to and beyond regional lymph nodes, complete eradication of the tumor by surgical intervention is nearly impossible (S. A. Rosenberg, Cancer: Principles and Practice of Oncology, V. T. Devita, S. Hellman and S. A. Rosenberg, Eds. (Lippincott-Raven, Philadelphia, 1997), p. 295). Instead, the whole body must be treated with radiation or chemotherapy, which are notoriously toxic to normal cells and tissues (V. T. Devita, Cancer: Principles and Practice of Oncology, V. T. Devita, S. Hellman and S. A. Rosenberg, Eds. (Lippincott-Raven, Philadelphia, 1997), p. 333). These facts underscore the need to identify the fundamental causes of metastasis and to translate this information into more effective and less toxic therapies. In spite of recent advances in studies of the basic mechanisms of metastasis, relatively little of this progress has translated into therapeutic approaches that minimize damage to normal tissues.

Metastasis

Recent investigation reveals that micrometastatic tumors can disseminate throughout the body long before cancer is first detected (D. E. Henson, et al, Current Opinion in Oncology 11:419, 1999) (I. J. Fidler, Cancer: Principles and Practice of Oncology, V. T. Devita, S. Hellman and S. A. Rosenberg, Eds. (Lippincott-Raven, Philadelphia, 1997), p. 135). This fact underscores the need to identify the causes of micrometastasis, with the ultimate goal of translating this information into new therapies. Growth and survival of benign and metastatic cells are differentially regulated by extracellular matrix (ECM) adhesion (J. A. Lawrence, et al., World Journal of Urology 14:124, 1996). Specifically, the growth and survival of benign epithelial cells requires cell attachment to the basal lamina. At the biochemical level, ECM anchorage generates signals that are necessary for growth and survival (E. Ruoslahti, Advances in Cancer Research 76:1, 1999). Consequently, the growth and survival of benign cells are compromised when they detach from the basement membrane or are transplanted into a foreign microenvironment (S. M. Frisch, et al., Current Opinion in Cell Biology 9:701, 1997). In contrast, metastatic cells grow and survive independent of changes in the local microenvironment (J. A. Lawrence et al., 1996). Unfortunately, most studies of metastatic cell growth and survival rely upon monolayer cell culture and thus fail to exploit important differences between normal and metastatic cells. Indeed, increasing evidence reveals that monolayer culture does not reliably model tumor cell behavior in vivo (J. A. Lawrence et al., World Journal of Urology 14:124 (1996)(V. M. Weaver, et al., Semin Cancer Biol 6: 175, 1995).

Cancer Cell Signaling

Cancer is a disease of aberrant signal transduction. Aberrant cell signaling overrides anchorage-dependent constraints on cell growth and survival (J. S. Rhim, et al., Critical Reviews in Oncogenesis 8:305, 1997; R. Patarca, Critical Reviews in Oncogenesis 7:343, 1996; R. K. Malik, et al., Biochimica et Biophysica Acta 1287:73, 1996); (W. G. Cance, et al., Breast Cancer Res Treat 35:105, 1995). Tyrosine kinase activity is induced by ECM anchorage and indeed, the expression or function of tyrosine kinases is usually increased in malignant cells (J. S. Rhim, et al., Critical Reviews in Oncogenesis 8:305, 1997; W. G. Cance, et al., Breast Cancer Res Treat 35:105, 1995; T. Hunter, Cell 88:333, 1997). Based on evidence that tyrosine kinase activity is necessary for malignant cell growth, tyrosine kinase have been targeted with new therapeutics (A. Levitzki, et al., Science 267:1782, 1995; B. S. Kondapaka, et al., Molecular & Cellular Endocrinology 117:53, 1996; D. W. Fry, et al., Current Opinion in Biotechnology 6: 662, 1995). Unfortunately, obstacles associated with specific targeting to tumor cells often limits the application of these drugs. In particular, tyrosine kinase activity is often vital for the function and survival of benign tissues (A. Levitzki, et al., Science 267:1782, 1995). To minimize collateral toxicity, it is critical to identify and then target tyrosine kinases that are selectively overexpressed in tumor cells.

New technologies to identify tyrosine kinases that are overexpressed or functionally altered in metastatic carcinoma cells are available (M. S. Kinch, et al., Hybridoma 17:227, 1998). Strategies were used to generate monoclonal antibodies against tyrosine kinases and their substrates in avian fibroblasts (S. B. Kanner, et al., Proc Nad Acad Sci USA 87:3328, 1990; J. R. J. Glenney, et al., J Cell Biol 108:2401, 1989). A small number of antigens were identified in these earlier studies. RIMMS immunization strategy was used to increase the breadth and sensitivity of monoclonal antibody production to generate monoclonal antibodies against tyrosine kinases in human breast carcinoma cells (Kinch et al., 1997, which is incorporated herein by reference in its entirety for the RIMMS method). RIMMS involves repetitive immunizations with low-dose antigen into multiple sites, all of which are proximal to draining lymph nodes. An abbreviated course of immunization promoted affinity maturation while minimizing immunodominance. RIMMS allowed us to isolate numerous monoclonal antibodies that recognize tyrosine kinases and their substrates in metastatic cells. The antibodies were screened for antigens that were differentially expressed in non-transformed versus metastatic epithelial cells. Two antibodies, D7 and B2D6, were identified that recognized an antigen that was grossly overexpressed and functionally altered on breast and prostate cancer cells (N. D. Zantek, et al, Cell Growth & Differentiation 10:629, 1999; J. Walker-Daniels, et al, Prostate 41: 275, 1999). The antigen was identified with a phage-expression library as the EphA2 tyrosine kinase.

EphA2

EphA2 is a 130 kDa receptor tyrosine kinase that is expressed in adult epithelia, where it is found at low levels and is enriched within sites of cell—cell adhesion (N. D. Zantek, et al, Cell Growth & Differentiation 10:629, 1999; R. A. Lindberg, et al., Molecular & Cellular Biology 10: 6316, 1990). This subcellular localization is important because EphA2 binds ligands (known as EphrinsA1 to A5) that are anchored to the cell membrane (J. G. Eph Nonmenclature Committee (Flanagan, N. W. et al., Cell 90, 403 (1997; N. W. Gale, et al., Cell & Tissue Research 290: 227, 1997). The Ephrin ligands, in turn, can bind any of 8 different EphA family kinases. The primary consequence of ligand binding is EphA2 autophosphorylation (R. A. Lindberg, et al., 1990). However, unlike other receptor tyrosine kinases, EphA2 retains enzymatic activity in the absence of ligand binding or phosphotyrosine content (N. D. Zantek, et al., 1999). Consequently, we define ligand-mediated "activation" as increased EphA2 phosphotyrosine content (N. D. Zantek, et al., 1999). Because most Eph kinase family members are expressed in the embryonic nervous system (E. B. Pasquale, Current Opinion in Cell Biology 9:608, 1997), investigators studying Eph kinases have largely overlooked EphA2, which is primarily on adult epithelial cells (R. A. Lindberg, et al., 1990). Studies of EphA2 have been further limited by a lack of reagents and model systems.

SUMMARY OF THE INVENTION

EphA2 receptor tyrosine kinase is grossly overexpressed and functionally altered in a large number of malignant carcinomas. EphA2 is a powerful and pervasive oncoprotein and EphA2 overexpression is sufficient to confer metastatic potential. Unique features of EphA2 in metastatic cells provide an extraordinary opportunity for therapeutic targeting of cancer.

The monoclonal antibodies of the present invention target the extracellular domain of EphA2 and operate to redirect the function of EphA2 to selectively block the growth and invasiveness of metastatic cells. The invention thus makes possible therapeutic strategies that optimally target metastatic cells while preventing collateral damage to normal tissues. This advance is expected to have a positive impact on cancer treatment and, as a result, increase survival and quality of life.

Thus, the invention relates to a monoclonal antibody, a fragment thereof, or a molecular complex thereof that binds to an extracellular domain of an EphA2 receptor molecule, wherein binding of the monoclonal antibody or fragment thereof to the EphA2 receptor molecule present in the membrane of a cancer cell favorably alters activity of the EphA2 receptor molecule. The invention further relates to methods of making and using the monoclonal antibodies and fragments.

BRIEF DESCRIPTION OF THE DRAWINGS

The accompanying drawings, which are incorporated in and constitute a part of this specification, illustrate (one) several embodiment(s) of the invention and together with the description, serve to explain the principles of the invention.

DETAILED DESCRIPTION

Figure 1:
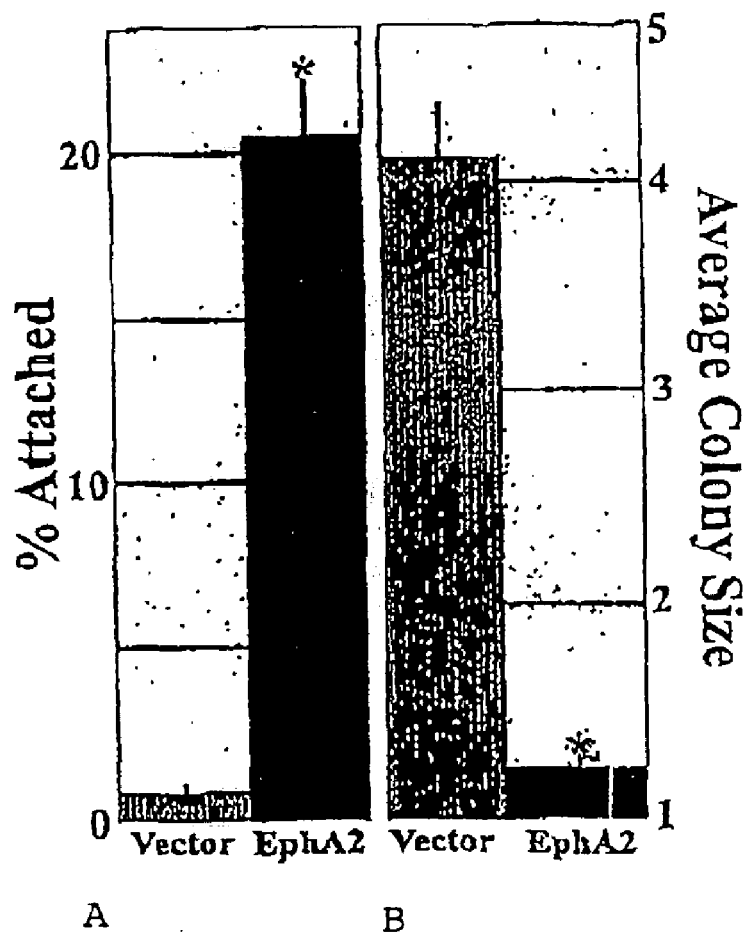
FIG. 1A shows the percentage of cells that remain attached in assays of ECM attachment, which were performed by incubating cells onto purified ECM for 30 min at 37 degrees, then vigorously washing and counting the adherent cells.
FIG. 1B shows the average size of the cell—cell aggregates in suspension. Asterisks denote that EphA2 overexpressing cells had statistically significant increases in ECM contacts ($P<4\times10^{-4}$) and decreased cell—cell adhesions ($P<3\times10^{-5}$) adhesions.

The present invention may be understood more readily by reference to the following detailed description of preferred embodiments of the invention and the Examples included therein and to the Figures and their previous and following description.

Before the present compounds, compositions, articles, devices, and/or methods are disclosed and described, it is to be understood that this invention is not limited to specific antibodies, specific hybridomas, or to particular methods, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "an antibody" includes mixtures of antibodies, reference to "a pharmaceutical carrier" includes mixtures of two or more such carriers, and the like.

Ranges may be expressed herein as from "about" one particular value, and/or to "about" another particular value. When such a range is expressed, another embodiment includes- from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not. For example, the phrase "optionally obtained prior to treatment" means obtained before treatment, after treatment, or not at all.

As used throughout, by "subject" is meant an individual. Preferably, the subject is a mammal such as a primate, and, more preferably, a human. The term "subject" includes domesticated animals, such as cats, dogs, etc., livestock (e.g., cattle, horses, pigs, sheep, goats, etc.), and laboratory animals (e.g., mouse, rabbit, rat, guinea pig, etc.).

The invention provides an antibody or fragment thereof that binds to an extracellular domain of an EphA2 receptor molecule, wherein binding of the monoclonal antibody or fragment thereof to the EphA2 receptor molecule present in the membrane of a cancer cell favorably alters activity of the EphA2 receptor molecule. In one embodiment, the antibody has the same epitope specificity as hybridoma B13, which was deposited Sep. 18, 2001 by Katherine E. Kilpatrick, on behalf of GlaxoSmithKline PLC, with the American Type Culture Collection, Rockville, Md. The deposit was assigned ATCC Accession Number PTA-3711. The description of the deposited material was "monoclonal antibody reactive with the tyrosine kinase receptor EphA2 derived from somatic fusion of mouse lymphocytes with the murine myeloma cell line P3BC1-2-13," with the strain designation EphA2 B13.46 and the attorney docket number as PH4265. Thus, in a preferred embodiment, the antibody is a monoclonal antibody. More specifically, the antibody is a monoclonal antibody produced by the B13 hybridoma. The antibody is raised to EphA2 from any species, including, for example, human, pig, guinea pig, dog, or rabbit. Preferably the antibody is raised to human EphA2.

The antibody of the invention in one embodiment is specific. Preferably, the antibody competes for binding with a natural ligand of the EphA2 receptor molecule. Examples of natural ligands include, for example, an ephrin.

As used throughout, "EphA2" includes the full length polypeptide, variants of EphA2, fusion proteins comprising EphA2, and immunogenic fragments of EphA2. Thus, the antibody binds full length EphA2, variants of EphA2 (e.g., an alternatively spliced variant), a fusion protein, or any epitope thereon. The EphA2 to which the antibody is raised is naturally occurring or recombinant. The antibody can be used in techniques or procedures such as diagnostics, screening, or imaging. Anti-idiotypic antibodies and affinity matured antibodies are also considered to be part of the invention.

As used herein, the term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The constant domains are not involved directly in binding an antibody to an antigen, but exhibit various effector functions, such as participation of the antibody in antibody-dependent cellular toxicity.

As used herein, the term "antibody or fragments thereof" encompasses chimeric antibodies and hybrid antibodies, with dual or multiple antigen or epitope specificities, and fragments, such as F(ab')2, Fab', Fab and the like, including hybrid: fragments. Thus, fragments of the antibodies that retain the ability to bind their specific antigens are provided. For example, fragments of antibodies which maintain EphA2 binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522–525 (1986); Riechmann et al., Nature, 332:323–327 (1988); and Presta, Curr. Op. Struct. Biol., 2:593–596 (1992)).

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., Nature, 321:522–525 (1986); Riechmann et al., Nature, 332:323–327 (1988); Verhoeyen et al., Science, 239:1534–1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody (Sims et al., J. Immunol., 151:2296 (1993) and Chothia et al., J. Mol. Biol., 196:901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding (see, WO 94/04679, published 3 Mar. 1994).

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., Proc. Natl. Acad. Sci. USA, 90:2551–255 (1993); Jakobovits et al., Nature, 362:255–258 (1993); Bruggemann et al., Year in Immuno., 7:33 (1993)). Human antibodies can also be produced in phage display libraries (Hoogenboom et al., J. Mol. Biol., 227:381 (1991); Marks et al., J. Mol. Biol., 222:581 (1991)). The techniques of Cote et al. and Boerner et al. are also available for the preparation of human monoclonal antibodies (Cole et al., Monoclonal Antibodies and Cancer Therapy, Alan R. Liss, p. 77 (1985); Boerner et al., J. Immunol., 147(1):86–95 (1991)).

The present invention further provides a hybidoma cell that produces the monoclonal antibody of the invention. The term "monoclonal antibody" as used herein refers to an antibody obtained from a substantially homogeneous population of antibodies, i.e., the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired activity (See, U.S. Pat. No. 4,816, 567 and Morrison et al., Proc. Natl. Acad. Sci. USA, 81:6851–6855 (1984)).

Monoclonal antibodies of the invention may be prepared using hybridoma methods, such as those described by Kohler and Milstein, Nature, 256:495 (1975) or Harlow and Lane. Antibodies, A Laboratory Manual. Cold Spring Harbor Publications, New York, (1988). In a hybridoma method, a mouse or other appropriate host animal, is typically immunized with an immunizing agent to elicit lymphocytes that produce or are capable of producing antibodies that will specifically bind to the immunizing agent. Alternatively, the lymphocytes may be immunized in vitro. Preferably, the immunizing agent comprises EphA2. Traditionally, the generation of monoclonal antibodies has depended on the availability of purified protein or peptides for use as the immunogen. More recently DNA based immunizations have shown promise as a way to elicit strong immune responses and generate monoclonal antibodies. In this approach, DNA-based immunization can be used, wherein DNA encoding a portion of EphA2 expressed as a fusion protein with human IgG1 is injected into the host animal according to methods known in the art (e.g., Kilpatrick K E, et al. Gene gun delivered DNA-based immunizations mediate rapid production of murine monoclonal antibodies to the Flt-3 receptor. Hybridoma. 1998 Dec; 17(6):569–76; Kilpatrick K E et al. High-affinity monoclonal antibodies to PED/PEA-15 generated using 5 microg of DNA. Hybridoma. 2000 Aug; 19(4):297–302, which are incorporated herein by referenced in full for the the methods of antibody production) and as described in the examples.

An alternate approach to immunizations with either purified protein or DNA is to use antigen expressed in baculovirus. The advantages to this system include ease of generation, high levels of expression, and post-translational modifications that are highly similar to those seen in mammalian systems. Use of this system involves expressing domains of EphA2 antibody as fusion proteins. The antigen is produced by inserting a gene fragment in-frame between the signal sequence and the mature protein domain of the EphA2 antibody nucleotide sequence. This results in the display of the foreign proteins on the surface of the virion. This method allows immunization with whole virus, eliminating the need for purification of target antigens.

Generally, either peripheral blood lymphocytes ("PBLs") are used in methods of producing monoclonal antibodies if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, "Monoclonal Antibodies: Principles and Practice" Academic Press, (1986) pp. 59–103). Immortalized cell lines are usually transformed mammalian cells, including myeloma cells of rodent, bovine, equine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies (Kozbor, J. Immunol., 133:3001 (1984); Brodeur et al., "Monoclonal Antibody Production Techniques and Applications" Marcel Dekker, Inc., New York, (1987) pp. 51–63).

The culture medium in which the hybridoma cells are cultured can then be assayed for the presence of monoclonal antibodies directed against EphA2. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art, and are described further in the Examples below or in Harlow and Lane "Antibodies, A Laboratory Manual" Cold Spring Harbor Publications, New York, (1988).

After the desired hybridoma cells are identified, the clones may be subcloned by limiting dilution or FACS sorting procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, protein G, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, plasmacytoma cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Optionally, such a non-immunoglobulin polypeptide is substituted for the constant domains of an antibody of the invention or substituted for the variable domains of one antigen-combining site of an antibody of the invention to create a chimeric bivalent antibody comprising one antigen-combining site having specificity for EphA2 and another antigen-combining site having specificity for a different antigen.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994, U.S. Pat. No. 4,342,566, and Harlow and Lane, Antibodies, A Laboratory Manual, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')2 fragment, that has two antigen combining sites and is still capable of cross-linking antigen.

The Fab fragments produced in the antibody digestion also contain the constant domains of the light chain and the first constant domain of the heavy chain. Fab'fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

An isolated immunogenically specific paratope or fragment of the antibody is also provided. A specific immunogenic epitope of the antibody can be isolated from the whole antibody by chemical or mechanical disruption of the molecule. The purified fragments thus obtained are tested to determine their immunogenicity and specificity by the methods taught herein. Immunoreactive paratopes of the antibody, optionally, are synthesized directly. An immunoreactive fragment is defined as an amino acid sequence of at least about two to five consecutive amino acids derived from the antibody amino acid sequence.

One method of producing proteins comprising the antibodies of the present invention is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the antibody of the present invention, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W. H. Freeman and Co., N.Y. (1992); Bodansky M and Trost B., Ed. (1993) Principles of Peptide Synthesis. Springer-Verlag Inc., NY. Alternatively, the peptide or polypeptide is independently synthesized in vivo as described above. Once isolated, these independent peptides or polypeptides may be linked to form an antibody or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776–779 (1994). The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini M et al. (1992) FEBS Lett. 307:97–101; Clark-Lewis I et al., J. Biol. Chem., 269:16075 (1994); Clark-Lewis I et al., Biochemistry, 30:3128 (1991); Rajarathnam K et al., Biochemistry 33:6623–30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity. (deLisle Milton R C et al., Techniques in Protein Chemistry IV. Academic Press, New York, pp. 257–267 (1992)).

The invention also provides fragments of antibodies which have bioactivity. The polypeptide fragments of the present invention can be recombinant proteins obtained by cloning nucleic acids encoding the polypeptide in an expression system capable of producing the polypeptide fragments thereof, such as an adenovirus or baculovirus expression system. For example, one can determine the active domain of an antibody from a specific hybridoma that can cause a biological effect associated with the interaction of the antibody with EphA2. For example, amino acids found to not contribute to either the activity or the binding specificity or affinity of the antibody can be deleted without a loss in the respective activity. For example, in various embodiments, amino or carboxy-terminal amino acids are sequentially removed from either the native or the modified non-immunoglobulin molecule or the immunoglobulin molecule and the respective activity assayed in one of many available assays. In another example, a fragment of an antibody comprises a modified antibody wherein at least one amino acid has been substituted for the naturally occurring amino acid at a specific position, and a portion of either amino terminal or carboxy terminal amino acids, or even an internal region of the antibody, has been replaced with a polypeptide fragment or other moiety, such as biotin, which can facilitate in the purification of the modified antibody. For example, a modified antibody can be fused to a maltose binding protein, through either peptide chemistry or cloning the respective nucleic acids encoding the two polypeptide fragments into an expression vector such that the expression of the coding region results in a hybrid polypeptide. The hybrid polypeptide can be affinity purified by passing it over an amylose affinity column, and the modified antibody receptor can then be separated from the maltose binding region by cleaving the hybrid polypeptide with the specific protease factor Xa. (See, for example, New England Biolabs Product Catalog, 1996, pg. 164.). Similar purification procedures are available for isolating hybrid proteins from eukaryotic cells as well.

The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment. These modifications can provide for some additional property, such as to remove or add amino acids capable of disulfide bonding, to increase its bio-longevity, to alter its secretory characteristics, etc. In any case, the fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antigen. (Zoller M J et al. Nucl. Acids Res. 10:6487–500 (1982).

A variety of immunoassay formats may be used to select antibodies that selectively bind with a particular protein, variant, or fragment. For example, solid-phase ELISA immunoassays are routinely used to select antibodies selectively immunoreactive with a protein, protein variant, or fragment thereof. See Harlow and Lane. Antibodies, A Laboratory Manual. Cold Spring Harbor Publications, New York, (1988), for a description of immunoassay formats and conditions that could be used to determine selective binding. The binding affinity of a monoclonal antibody can, for example, be determined by the Scatchard analysis of Munson et al., Anal. Biochem., 107:220 (1980).

Also provided is an antibody reagent kit comprising containers of the monoclonal antibody or fragment thereof of the invention and one or more reagents for detecting binding of the antibody or fragment thereof to the EphA2 receptor molecule. The reagents can include, for example, fluorescent tags, enzymatic tags, or other tags. The reagents can also include secondary or tertiary antibodies or reagents for enzymatic reactions, wherein the enzymatic reactions produce a product that can be visualized.

The invention also provides a molecular complex that binds to an extracellular domain of an EphA2 receptor molecule, wherein binding of the molecular complex to the EphA2 receptor molecule favorably alters the biological activity of the EphA2 receptor molecule, the molecular complex comprising a monoclonal antibody or fragment thereof linked to a therapeutic agent. The therapeutic agent is selected from the group consisting of a chemotherapeutic agent, a radiotherapeutic agent, an immunotherapeutic agent, and combinations.

Overexpression and functional alteration of EphA2 provide an extraordinary opportunity for antibody-based targeting of metastatic carcinoma cells. We have developed monoclonal antibodies that mimic the actions of ligand as a means of redirecting EphA2 function so that it blocks malignant cell growth and migration. In addition to their potential as therapeutic agents, these monoclonal antibodies are important research tools, because the artificial ligand (EphrinA1-$F_c$) is highly unstable, has a relatively low affinity for EphA2, cross-reacts with other EphA kinases, and induces only a transient biological response (which is related to its weak affinity and poor stability). Previously described EphA2 antibodies (e.g., B2D6, which binds the extracellular domain of EphA2, and D7, which binds the intracellular domain of EphA2) do not activate In one embodiment, the monoclonal antibody of the invention binds to the extracellular domain of a membrane-embedded EphA2 receptor molecule, thereby favorably altering its biological activity in a cancer cell, including, for example, a mammalian cancer cell. By "favorably altering the biological activity" of an EphA2 receptor in a cancer cell, it is meant that the activity, number (i.e., protein levels) and/or function of EphA2 receptors in cancer cells is changed so as to arrest or reverse cell growth or proliferation, or to initiate or cause killing of the cancer cell. Arrest or reversal of cell growth or proliferation can be evidenced by various phenotypic changes in the cancer cells such as increased differentiation, decreased affinity for ECM proteins, increased cell—cell adhesions, slower growth rate, reduced numbers of EphA2 and/or increased localization of EphA2, decreased cell migration or invasion, and can be caused either directly or indirectly.

It should be understood that the present invention is not to be limited by any particular mechanism by which or through which the EphA2 monoclonal antibodies favorably alter the biological activity of EphA2 in cancer cells; it is only required that the monoclonal antibodies bind to the extracellular domain of EphA2 and that binding results in a favorable change in EphA2 activity. Possible mechanisms that may account for the favorable change in EphA2 activity upon binding of a monoclonal antibody of the invention include, but are not limited to: (1) the monoclonal antibody may function as a natural ligand of EphA2, wherein the natural ligand prevents transformation or metastasis of the cell; (2) binding of the monoclonal antibody to EphA2 may cause degradation of EphA2, for example by proteosomal or lysosomal enzymes, which may in turn signal favorable changes in the phenotype of the cell; and (3) the monoclonal antibody may be immunogenic, such that binding of the monoclonal antibody to EphA2 may stimulate the subject's immune system, resulting in killing of the cancer cell; and (4) the monoclonal antibody may function as a carrier molecule for targeted delivery of a therapeutic agent, as described below.

In another embodiment of the invention, a monoclonal antibody that binds to the extracellular domain of the EphA2 receptor may be linked to a therapeutic agent, thereby forming a molecular complex to effect cancer cell death or stasis. The linkage is preferably covalent, but can also be noncovalent (e.g., ionic). Examples of therapeutic agents are chemotherapeutic agents, a radiotherapeutic agent, and immunotherapeutic agent, as well as combinations thereof. In this way, the "drug" (i.e., the molecular complex) delivered to the subject can be multifunctional, in that it exerts one therapeutic effect by binding to the extracellular domain of EphA2 and a second therapeutic by delivering a supplemental therapeutic agent. Binding the EphA2 receptor with the monoclonal antibody of the invention can cause internalization of the receptor, which is useful for introducing a therapeutic agent such as a toxin into a cancer cell.

It should be understood that the invention is not limited by the nature of the therapeutic agent linked to the monoclonal antibody; any therapeutic agent which is intended for delivery to the cancer cell can be complexed to the monoclonal antibody of the invention. The therapeutic agent can act extracellularly, for example by initiating or affecting an immune response, or it can act intracellularly, either directly by translocating through the cell membrane or indirectly by, for example, affecting transmembrane cell signaling. The therapeutic agent is optionally cleavable from the monoclonal antibody. Cleavage can be either autolytic, accomplished by proteolysis, or effected by contacting the cell with a cleavage agent. Examples of intracellular therapeutic agents include small molecule inhibitors of EphA2, ATP analogs, and agents that alter EphA2 protein stability, particularly agents that initiate, accelerate or cause degradation of EphA2.

The invention further provides various diagnostic and treatment methods. For example, a method of treating cancer in a subject is provided. Specifically, the method comprises administering to the subject a therapeutic amount of a treatment agent effective to favorably alter the biological activity of the EphA2 receptor molecule. The treatment agent comprises a monoclonal antibody or fragment thereof that binds to the extracellular domain of the EphA2 receptor molecule. In another embodiment, the treatment agent comprises a molecular complex, wherein the molcular complex comprises a monoclonal antibody or fragment thereof linked to a therapeutic agent and wherein the monoclonal antibody or fragment thereof binds to an extracellular domain of the EphA2 receptor molecule. In a preferred embodiment, the monoclonal antibody used in the treatment method has the same epitope specificity as hybridoma B13.

The method is effective to treat a cancer characterized by cells having overexpressed or functionally altered EphA2 receptors, preferably metastatic carcinoma of the breast, prostate, colon, lung, bladder, ovary, pancreas and skin (e.g., melanoma). Thus, the types of cancer to be treated include cancers comprising one or more metastatic carcinoma cells or tumor cells, including primary tumor cells. A treatment agent that favorably alters the biological activity of EphA2 on these cells is introduced into the subject, either systemically or at the site of a cancer tumor, in an amount effective to alter the biological activity of EphA2. Preferably, the treatment agent comprises a monoclonal antibody that binds to the extracellular domain of EphA2. In a preferred embodiment, the treatment is an EphA2 monoclonal antibody or a molecular complex comprising an EphA2 monoclonal antibody linked to a therapeutic agent, as described above. Where the molecular complex includes a cleavable therapeutic agent, treatment can include delivery of a second therapeutic agent to effect cleavage.

It should be understood, however, that the treatment methods of the invention are not limited to the use of EphA2 monoclonal antibodies or molecular complexes containing EphA2 monoclonal antibodies; rather, the method includes treatment of the subject with any molecule that favorably alters the biological activity of EphA2. The inventors have shown that alteration of EphA2 activity according to the invention results in a desirable change in the phenotype of a cancer cell, and the therapeutic method of the invention thus encompasses the delivery of a variety of agents to a subject that induce or cause this favorable alteration in the biological activity of EphA2. For example, a proteinaceous intracellular agent that alters the activity of EphA2 can be delivered as a nucleic acid, for example as RNA, DNA, or analogs or combinations thereof, using conventional methods, wherein the therapeutic polypeptide is encoded by the nucleic acid and operably linked to regulatory elements such that it is expressed in the target cell.

The amount of antibody or fragment thereof administered or the schedule for administration will vary among individuals based on age, size, weight, condition, the mode of administration, the diagnosis and the severity of the condition to be treated. One skilled in the art will realize that dosages are best optimized by the practicing physician and methods for determining dosage are described, for example in Remington's Pharmaceutical Science, 16th ed., 1980, Mack Publishing Co., edited by Oslo et al. Guidance in selecting appropriate doses for antibodies is found in the literature on therapeutic uses of antibodies, e.g., Handbook of Monoclonal Antibodies, Ferrone et al., eds., Noges Publications, Park Ridge, N.J., (1985) ch. 22 and pp. 303–357; Smith et al., Antibodies in Human Diagnosis and Therapy, Haber et al., eds., Raven Press, New York (1977) pp. 365–389. A typical dose of the antibody used alone might range from about 1 µg/kg to up to 100 mg/kg of body weight or more per day, and preferably 1 µg/kg to up to 1 mg/kg, depending on the factors mentioned above. An intravenous injection of the antibody or fragment thereof, for example, could be 10 ng–1 g of antibody or fragment thereof, and preferably 10 ng–1 mg depending on the factors mentioned above. For local injection, a typical quantity of antibody ranges from 1 pg to 1 mg. Preferably, the local injection would be at an antibody concentration of 1–100 µg/ml, and preferably 1–20 µg/ml.

In vivo and in vitro methods of diagnosing cancer are also provided. The diagnostic method of the invention can be used to obtain or confirm an initial diagnosis of cancer, or to provide information on cancer localization, cancer metastasis, or cancer prognosis. In one embodiment of the method, cancer is diagnosed in vivo by administering to a subject an EphA2 monoclonal antibody or a molecular complex comprising an EphA2 monoclonal antibody linked to a diagnostic agent. The antibody or molecular complex can be administered systemically or locally. Specifically, the method comprises the steps of administering to the subject an EphA2 monoclonal antibody or a fragment thereof or administering to the subject a molecular complex comprising the EphA2 monoclonal antibody or fragment thereof linked to a diagnostic agent, wherein the monoclonal antibody or fragment thereof binds to an extracellular domain of an EphA2 receptor molecule and wherein the diagnostic agent comprises a detectable label; and detecting the EphA2 monoclonal antibody, the fragment thereof, or the molecular complex at a site within the subject, wherein the presence of the EphA2 monoclonal antibody, the fragment thereof, or the molecular complex at the site is indicative of cancer at that site. The detection step can be performed using a noninvasive medical technique such as radiography, fluoroscopy, sonography, imaging techniques such as magnetic resonance imaging, and the like.

The in vitro method of diagnosing cancer in a subject is also provided. The steps of the method comprise contacting a biological sample from the subject with an EphA2 monoclonal antibody or fragment thereof or contacting the biological sample with a molecular complex comprising the EphA2 monoclonal antibody linked to a diagnostic agent, wherein the monoclonal antibody or fragment thereof binds to an extracellular domain of an EphA2 receptor molecule and wherein the diagnostic agent comprises a detectable label; and detecting the EphA2 monoclonal antibody, the fragment thereof, or the molecular complex bound to the biological sample, wherein binding of the EphA2 receptor molecule or the molecular complex to the biological sample indicates the presence of cancer in the biological Bound monoclonal antibody, fragment, or complex can be detected directly in an ELISA or similar assay; alternatively, the diagnostic agent can comprise a detectable label, and the detectable label can be detected using methods known in the art.

Also provided are methods of making the monoclonal antibody of the invention. In a preferred method, the method comprises the steps of introducing a nucleic acid immunogen into an animal, wherein the nucleic acid immunogen comprises a nucleic acid encoding an extracellular domain of an EphA2 receptor molecule fused with a nucleic acid encoding an human immunoglobulin or fragment thereof; removing lymphocytes from the animal; somatically fusing the lymphocytes with a myeloma cell to yield a hybridoma cell that secretes the monoclonal antibody, and isolating the monoclonal antibody. In one embodiment, the nucleic acid immunogen is introduced in to epidermal dendritic cells of the animal. It should be understood that EphA2 monoclonal antibodies of the invention can be made using other hybridoma techniques, for example by immunizing a mouse with a polypeptide immunogen and utilizing mouse splenocytes in the cell fusions.

Also provided is a method of making the molecular complex of the invention. Although there are a variety of ways to make the molecular complex, one method comprises linking a therapeutic agent and a monoclonal antibody or fragment thereof, wherein the monoclonal antibody or fragment thereof binds to an extracellular domain of an EphA2 receptor molecule.

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in degrees C or is at ambient temperature, and pressure is at or near atmospheric.

EXAMPLES

The present invention is illustrated by the following examples. It is to be understood that the particular examples, materials, amounts, and procedures are to be interpreted broadly in accordance with the scope and spirit of the invention as set forth herein.

Example 1

E-Cadherin Regulates the Function of the EphA2 Receptor Tyrosine Kinase

The localization and phosphorylation of EphA2 in mammary epithelial cells was dependent on E-cadherin-mediated adhesion and that loss of E-cadherin in metastatic tumor cells causes alterations in EphA2 localization and phosphorylation. In addition, the experimental induction of EphA2 phosphorylation decreased cell-ECIVI attachment at focal adhesions and negatively regulated the proliferation of metastatic cells.

Cell Lines and Antibodies

Human breast carcinoma cells and non-transformed human marrimary epithelial cell lines were cultured as described previously (Kinch. M. S., et al. E-cadherin engagement stimulates tyrosine phosphorylation. Cell Adhes. Commun., 4: 425–437, 1997; Bale. S. N., Molecular and cellular analysis of basement membrane Invasion by human breast cancer cells in Matrigal-based in vitro assays. Breast Cancer Res. Treat, 24: 241–255, 1993). We purchased antibodies specific for E-cadherin (polyclonal antibodies, Transduction Laboratories, Lexington, Ky.; and DECMA-1, Sigma Chemical Co., St. Louis. Mo.). phosphotyrosine (PY20. ICN, Costa Mesa, Calif.: 4G10, Upstate Biotechnology Inc., Lake Placid. N.Y. and polyclonal antibodies, Transduction Laboratories), and fluorescein-conjugated BrdUrd (Harian Sera-Lab Ltd., Loughborough. United Kingdom). Monoclonal antibodies specific for EphA2 (clones D7 and B2D6) were produced in the laboratory as described (Kinch. M. S. et al. Identification of tyrosine phosphorylated adhesion proteins in human cancer cells. Hybridoma, 17. 227–235, 1998) or purchased from Upstate Biotechnology Inc. Rabbit polyclonal antibodies for EphA2 were purchased from Santa Cruz Biotechnology, Inc. (Santa Cruz. Calif.). EKI 66B monoclonal EphA2 antibodies were generously provided by R. Lindberg (Amgen. Thousand Oaks. Calif.). Paxillin-specific antibodies were obtained from K Burridge (University of North Carolina, Chapel Hill, N.C.). To visualize f-actin, we used fluorescein-conjugated phalloidin purchased from Molecular Probes (Eugene, Oreg.).

Western Blot Analysis

Unless noted otherwise, all experiments used confluent cell monolayers that were extracted in a buffer containing 1% Triton X-100 or in RIPA buffer containing 1% Triton X-100, 0.5% sodium deoxycholate, and 0.1% SDS for 6 min on ice, as described previously (Kinch, M. S., et al. 1995). After protein concentrations were measured by Coomassie Blue staining (Pierce, Rockford. Ill.) or Bio-Rad Protein Assay (Hercules, Calif.), equal amounts of protein were resolved by SDS-PAGE and transferred to nitrocellulose (Protran, Schleicher & Schuell, Keene, N.H.), and Western blot analysis was performed as described previously (Kinch, M. S., et al. 1995). Antibody binding was detected by enhanced chemiluminescence as recommended by the manufacturer (Pierce). To reprobe, the blots were stripped as described previously (Kinch, M. S., et al. 1995).

Immunofluorescence and Confocal Microscopy

Immunostaining was performed as described previously (Kinch, M. S., et al. 1995). In brief, cells were grown on glass coversfips to visualize individual cells—Cells were observed at both high cell density (approximately 70% confluence) and low cell density (approximately 20% confluence) by seeding $1 \times 10^5$ cells onto either a 3.5- or 10-cm tissue culture plate overnight at 37° C. At high cell density, extensive overlapping of neoplastic cells precludes accurate subcellular visualization. The samples were fixed in 3.7% formaldehyde solution, extracted in 0.5% Triton X-100, and stained. Immunostaining was visualized using rhodamine-conjugated donkey antimouse antibodies (Chemicon, Temecula. CN) and FITC-conjugated donkey antirabbit (Chemicon) and epifluorescence microscopy (model BX60×600, Olympus Lake Success, N.Y.) and recorded onto T-Max 400 film (Eastman-Kodak, Rochester, N.Y.). For confocal microscopy, samples were viewed on a Nikon Diaphot 300 outfitted with a Bio-Rad MRC 1024 UV/Vis System and Coherent Innova Enterprise model 622 60-mW output water-cooled lasers.

Immunoprecipitation

Immunoprecipitation experiments were performed as described (Kinch, M. S., et al. 1995) for 1.5 h at 4° C. with the appropriate EphA2-specific monoclonal antibodies (D7 or B2D6) and rabbit antimouse (Chemicon) conjugated protein A-Sepharose (Sigma). Immunoprecipitates were washed three times in lysis buffer, resuspended in SDS sample buffer (Tris buffer containing 5% SDS, 3.8% DTT, 25% glycerol. and 0.1 % bromphenol blue), and resolved by 10% SDS-PAGE.

In Vitro Kinase Assays

For in vitro autophosphorylation assays, immunoprecipitated EphA2 was washed in lysis buffer and incubated in 10 mM PIPES, 3mM $MnCl_2$, 5 mM PNPP (Sigma 104 phosphatase substrate, Sigma), 1 mm $NaVO_4$, 1 μm ATP, and 10 μCi of $-^{32}P$ (New England Nuclear, Boston, Mass.) at 25° C. for the times shown. The reactions were terminated by the addition of 5× Laemmli sample buffer at multiple time points before saturation. After resolving samples by 10% SDS-PAGE, the gel was transferred to nitrocellulose (Schleicher & Schuell) or Immobilon P (Pierce), and incorporated material was detected by autoradiography. To hydrolyze phosphoserine/threonine, the membranes were treated with 1 N KOH at 65° C. for 1 h and reassessed by autoradiography. After several half-lives, Western blot analysis was performed to determine EphA2 loading.

Cross-Linking of EphA2 Receptors

For antibody cross-linking experiments, cells grown as a monolayer were incubated at 4° C. for 20 min with 4 μg/ml EphA2 antibody (for example, either clone EK 166B, B2D6 or B13) or purified fusion protein of ephrin-A1 fused to IgG (B61-IgG) (Pandey, et al., 1995). Primary antibody alone, rabbit antimouse IgG alone and control fusion proteins were used as controls. The samples were washed with medium, incubated with 20 μg/ml rabbit antimouse IgG in conditioned medium at 4° C. for 10 min. and warmed to 37° C. for 10 min before extraction and immunoprecipitation. To determine the optimal time for activation, the plates were incubated in the presence of cross-linking antibody at 37°0 for 0–120 min.

EGTA and Antibody Treatments

"Calcium switch" experiments were performed as described previously (Kinch, et al., 1997). Monolayers of MCF-10 A cells were grown to about 80% confluence. EGTA was added to growth medium to a final concentration of 4 mm, and the cells were incubated at 37° C. for 30 min. The medium was removed, and calcium concentrations restored with normal growth medium. To block E-cadherin function, the medium was supplemented with E-cadherin antibodies (1:100 dilution; DECMA-1; Sigma) or 10 μg/ml peptide corresponding to the E-cadherin HAV sequence (YTLFSHAVSSNGN (SEQ ID NO:1)). Controls include isotype control antibodies (rat anti-HA antibody; Boehringer Mannheim, Indianapolis, Ind.) and matched, scrambled peptides (SGATNSLHNFSVY (SEQ ID NO:2)). The Purdue Laboratory for Macromolecular Structure synthesized the peptides. Cells were then incubated for the indicated times at 37° C. and extracted for Western blot analysis and immunoprecipitation. Cell monolayers grown on glass coverslips were treated in the same manner and immunostained for EphA2.

E-Cadherin Expression and Function

MDA-MB-231 cells were co-transfected with pBATEM2, a mouse E-cadherin expression vector (Nose, A., et al. Expressed recombinant cadherins medlatd cell sorting in model systems. Cell. 54:993–1001, 1988) and pSV2neo (Southern, P. J., et al. Transformation of mammalian calls to antibiotic resistance with a bacterial gene under control of the SV40 early region promoter. J. Mol. Appl. Genet., 1: 327–341, 1982) using FuGENE 6 Transfection Reagent (Boehringer Mannheim), following the manufacturer's instructions. Transfected cells were selected in growth media supplemented with 400 μg/ml G418. Immunostaining and Western blot analysis with specific antibodies confirmed E-cadherin expression.

Proliferation Assay

Cells were plated onto glass coverslips and cultured overnight in growth medium. EphA2 antibodies (EK166B, B2D6, or B13, extracellular, or D7, intracellular) or ligand fusion protein (B61-IgG) were added to the media at 1 μg/ml and incubated at 4° C. for 20 min, washed with medium, and incubated with 20 μg/ml rabbit antimouse plus 3 μg/ml BrdUrd at 37° C. for 4 h. Cells were fixed in cold methanol for 8 min, extracted with 2 N HCl at 37° C. for 30 min and stained with a BrdUrd antibody to indicate proliferating cells and Hoechst dye to label the nuclei of all cells on the coverslip. A minimum of six random fields were selected in a double-blind study, and at least 150 cells were assessed in each sample. Each experiment was repeated at least three times.

Statistical Methods

All statistical analyses were performed using the SAS System for Windows, Version 6.12. An ANOVA model was used to compare the percentage of cells that grew in each field, within each specimen, In the control group to the percentage of cells that grew in each field, within each specimen, in the experimental group. Group (control versus experimental) was treated as a fixed effect and specimen within each group was treated as a random effect. A normal probability plot of the residuals was used to assess the homogeneity of the variances of the mean percentage cell growth for the control and experimental groups. $P<0.05$ was considered statistically significant.

Regulation of EphA2 Expression in Breast Cancer Cells

EphA2 expression levels were measured in breast epithelial cell lines derived from nonneoplastic epithelia (e.g., MCF-10A, MCF-12A, and MCF-10-2; Paine, T. M., et al. Characterization of epithelial phenotypes in mortal and immortal human breast cells. Int. J. Cancer, 50: 463–473, 1992; Pauley, R. J., et al. The MCF10 family of spontaneously immortalized human breast epithelial cell lines: models of neoplastic progression. Eur. J. Cancer Prev. 2 (Suppl. 3): 67–76, 1993) and metastatic breast cancer (e.g., MDA-MB-231 and MDA-MB-435; Price, J. E. Metastasis from human breast cancer cell lines. Breast Cancer Res. Treat., 39: 93–102, 1996; Zhang, R. et al., Relative malignant potential of human breast carcinoma cell lines established from pleural effusions and a brain metastasis. Invasion Metastasis, 11: 204–215, 1991). EphA2 from whole cell lysates or immunoprecipitated from monolayers of nonneoplastic (MCF-10A, MCF10-2, and MCF-12A) and metastatic (MDA-MB231 and MDA-MB-435) breast cancer call lines was resolved by SDS-PAGE and Western blot analysis performed with EphA2 antibodies. The blot was stripped and reprobed with phosphotyrosine-specific (PY20) antibodies. Tyrosine-phospherylated EphA2 was absent in metastatic breast cancer cells. EphA2 was found to be expressed in nontransformed mammary epithelial and metastatic breast cancer cell lines tested with 2-5-fold more EphA2 in neoplastic cells, as determined by Western blot analysis using multiple EphA2 antibodies and by Northern blot analysis.

Despite its overexpression, EphA2 in metastatic cells displayed a much-reduced phosphotyrosine content. For these studies, EphA2 was immunoprecipitated from confluent monolayers of either nonneoplastic or metastatic cells and Western blot analysis performed with phosphotyrosine specific antibodies. This revealed prominent phosphorylation of EphA2 in nonneoplastic cells, whereas the EphA2 from metastatic cells was not tyrosine-phosphorylated. The decreased phosphotyrosine content was confirmed using different EphA2 antibodies (D7, B2D6, and rabbit polyclonal antibodies) for immunoprecipitation and with multiple phosphotyrosine antibodies (PY20, 4G10, and rabbit polyclonal antibodies) for Western blot analysis. Decreased EphA2 phosphorylation was also observed in other metastatic breast cancer cell lines as well as invasive tumor cell lines derived from colon, pancreatic, ovarian, and lung cancers.

Further comparison of EphA2 in nonneoplastic and metastatic cells revealed other changes in EphA2 distribution and function. The subcellular distribution of EphA2 in nontransformed mammary epithelial cells (MCF-10A) and metastatic breast cancer cells (MDA-MB-231) was assessed by immunostaining with EphA2-specific antibodies. The cells were plated at either high or low cell density to emphasize the localization of EphA2 within cell—cell contacts or membrane ruffles of nontransformed or invasive cells, respectively. Immunofluorescence staining with EphA2-specific antibodies revealed that EphA2 in nonneoplastic cells was mostly found within sites of cell—cell contact, with little staining of membrane that was not in contact with neighboring cells. In contrast, EphA2 in metastatic cells was absent from sites of cell—cell contacts. Instead, the EphA.2 in these cells was either diffusely distributed or enriched within membrane ruffles at the leading edge of migrating cells. The enrichment within membrane ruffles was confirmed by colocalization of EphA2 with f-actin. This localization within membrane ruffles was not observed in nontransformed epithelia, even at low cell density. These differences in subcellular distribution were confirmed using three different EphA2-specific antibodies (D7, 82D6, and rabbit polyclonal antibodies).

EphA2 Enzymatic Activity in Metastatic Cells

Tyrosine phosphorylation of a kinase often regulates enzymatic activity. To test the effect of differences in EphA2 phosphorylation on kinase activity, EphA2 autophosphorylation was measured using in vitro kinase assays with immunoprecipitated material. The enzymatic activity of EphA2 was measured using an in vitro autophosphorylation assay. At 2, 4, or 8 minutes, the in vitro reaction was terminated and resolved by SDS-PAGE. The blot was treated with KOH to hydrolyze phosphoserine and phosphothreonine prior to autoradiography. After several half-lives, Western blot analysis was performed with EphA2 antibodies to confirm equal sample loading. Despite the low phosphotyrosine content of EphA2 in metastatic cells, this EphA2 demonstrated enzymatic activity that was comparable with or higher than the activity of EphA2 isolated from nonneoplastic cells. This activity was unaffected by the basal phosphotyrosine content of EphA2 because unlabeled phosphate was rapidly exchanged with labeled phosphate during the autophosphorylation assays as described previously (Foulkes. J. G., et al. Purification and characterization of a protein-tyrosine kinase encoded by the Abelson murine leukemia virus. J. Biol. Chem., 260: 8070–8077, 1985; Hutchcroft, J. E. B lymphocyte activation is accompanied by phosphorylation of a 72-kDa protein-tyrosine kinase. J. Biol. Chem., 266: 14846–14849, 1991). KOH treatment of the membranes prior to autoradiography did not significantly reduce the level of phosphorylation, indicating that the observed enzymatic activity represented mostly phosphorylation on tyrosine residues. It is also notable that the phosphotyrosine content of EphA2 was not predictive of its enzymatic activity.

EphA2 was identified using antibodies that recognize tyrosine-phosphorylated proteins in Ras-transformed MCF-10A-neoT cells (Kinch. M. S. et al. Identification of tyrosine phosphorylated adhesion proteins in human cancer cells.

Hybridoma, 17. 227–235, 1998). MCF-10A-neoT cells express E-cadherin (Kinch. M. S. et al. Identification of tyrosine phosphorylated adhesion proteins in human cancer cells. Hybridoma, 17. 227–235, 1998) and, consequently, EphA2 is tyrosine-phosphorylated. Notably, EphA2 was tyrosine-phosphorylated in nonneoplastic mammary epithelial cell lines but not in metastatic cell lines. In this respect, EphA2 differs from many other tyrosine kinases (e.g., cErbB2, epidermal growth factor receptor, platelet-derived growth factor receptor, and Src), the phosphorylation of which increases in cancer cells (Cance, W. G., et al. Protein kinases In human breast cancer. Breast Cancer Res. Treat., 35: 105–114, 1995; Press, M. F., et al. HER-21neu oncogene amplification and expression in breast and ovarian cancers. Prog. Clin. Blot. Res., 354A: 209–221, 1990; Murphy. L. C., et al. Epidermal growth factor gene expression in human breast cancer cells: regulation of expression by progestins. Cancer Res., 43: 4555–4560. 1988). For these kinases, phosphorylation elevates tyrosine kinase activity, triggering signal transduction cascades that promote cell proliferation.

The phosphotyrosine content of EphA2 does not relate to its intrinsic enzymatic activity in mammary epithelial cells. In vitro assays revealed that, despite its low phosphotyrosine content, the enzymatic activity of EphA2 in metastatic cells is comparable with or increased over the activity of phosphorylated EphA2 in nonneoplastic epithelial cells. This is consistent with evidence that the phosphorylation of EphB2 also has little effect on its kinase activity (Murphy. L. C., Epidermal growth factor gene expression in human breast cancer cells: regulation of expression by progestins. Cancer Res., 43: 4555–4560. 1988). Rather than controlling enzymatic activity, the phosphotyrosine content of EphA2 influences the choice or availability of substrates and interacting proteins. In addition, changes in the phosphotyrosine content of EphA2 might provide signals that are independent of EphA2 enzymatic activity, which is supported by recent reports that other Eph kinases (VAB-1 and EphB2) have kinase-independent functions (George, S. E., et al. The VAB-1 Eph receptor tyrosine kinase functions in neural and epithelial morphogenesis in C. elegans. Cell, 92: 633–643, 1998; Henkerneyer, M., et al. Nuk controls pathfinding of commissural axons in the mammalian central nervous system. Cell, 86: 35–46, 1996). Thus, protein interactions, localization, phosphotyrosine content, and enzymatic activity all contribute to Eph receptor function.

There are several possible explanations for the loss of EphA2 phosphorylation in metastatic cells. The primary sites of receptor autophosphorylation are not mutated because the sites that become autophosphorylated in vitro are the same in nontransformed and neoplastic cells. Consistent with this, EphA2 tyrosine phosphorylation was restored by cross-linking EphA2 with antibodies or by transfection with E-cadherin. Another possible cause for decreased EphA2 phosphorylation could be loss of EphA2 ligands (ephrin-A class molecules). However, the inability to restore EphA2 phosphorylation in E-cadherin-transfected cells excluded this possibility. A third possibility is that the phosphotyrosine content of EphA2 is repressed by an associated tyrosine-phosphatase. Consistent with this, treatment of neoplastic cells with tyrosine-phosphatase inhibitors restored normal levels of EphA2 tyrosine phosphorylation.

Receptor Aggregation Induces EphA2 Tyrosine Phosphorylatlon in Metastatic Cells

EphA2 in neoplastic cells retained the capacity to become activated. Immunoprecipitated EphA2 was subjected to Western blot analysis with phosphotyrosine antibodies (PY20) following aggregation of cell surface EphA2 for 5 min at 37° C. with specific primary and secondary antibodiesy. Simple engagement of anti-EphA2y or antimouse alone was insufficient to induce tyrosine phosphorylation above basal levels. The blot was then stripped and reprobed with EphA2 antibodies as a loading control. The time course of EphA2 phosphorylatlon was measured after cross-linking EphA2 in MDA-MB-231 cells for 0–60 min by Western blot analysis of immunoprecipitated EphA2 with phosphotyrosine-specific antibodies (PY20). EphA2 was aggregated using a soluble ligand fusion protein (B61-IgG). A control fusion protein served as a negative control, and B2D6-mediated aggregation served as a positive control for activation.

EphA2 tyrosine phosphorylation was induced by aggregation of EphA2 with a soluble form of ephrin-A (B61-IgG, a chimera of the EphrinA1 extracellular domain fused to immunoglobulin heavy chain; also known as a "ligandbody" (Pandey, A., et al., Role of B61, the ligand for the Eck receptor tyrosine kinase, in TNF-$\alpha$-induced angiogenesis. Science (Washington DC), 269: 567–569. 1995; Hutchcroft, J. E. B lymphocyte activation is accompanied by phosphorylation of a 72-kDa protein-tyrosine kinase. J. Biol. Chem., 266: 14846–14849, 1991). In contrast, a control chimera did not alter EphA2 phosphorylation. Clustering EphA2 at the cell surface with specific antibodies (EK166B or B2D6) also induced levels of EphA2 activation that were comparable with that nonneoplastic cells. Receptor aggregation, not simply antibody binding, was necessary for EphA2 phosphorylation as incubation with anti-EphA2 alone did not increase EphA2 phosphorylation relative to matched controls. This effect was specific for EphA2 as neither secondary antibodies alone or clustering of isotype-matched control antibodies (which recognize an inaccessible cytoplasmic epitope on EphA2) did not induce tyrosine phosphorylation of EphA2. Analysis of the timing of EphA2 phosphorylation revealed EphA2 phosphorylation within 2 min after cross-linking, with optimal phosphorylation detected after 5 min.

E-Cadherin Regulates EphA2 in Nontransformed Epithelia

Tyrosine phospharylation of EphA2 correlated with its localization within sites of cell—cell contact. Because Eph receptors become activated by ligands that are attached to the surface of neighboring cells (Gale, N. W., et al. Eph receptors and ligands comprise two major specificity subclasses and are reciprocally compartmentalized during embryogenesis. Neuron, 17: 9–19, 1996), stable cell—cell adhesions might be necessary for EphA2 activation. Adhesions mediated by E-cadherin generate the most stable interactions between epithelial cells. (Geiger, B., et al. Annu. Rev. Cell Biol., 8: 307–332, 1992), and EphA2 was not phosphorylated and was absent from intercellular contacts in cells lacking E-cadherin. These include metastatic cancer cells as well as nontransformed fibroblasts (e.g., NIH 3T3, REF-52, and C3H10T½) and myoepithelial cells (HBL-100). E-cadherin was tested to determine whether it regulated EphA2 phosphorylation. The subcellular distribution of EpKA2 and E-cadherin was evaluated in MCF-10A cells using two-color immunofluorescence microscopy.

Because both EphA2 and E-cadherin are found at sites of cell—cell contact, the two proteins were examined using two-color immunofluorescence microscopy to detect colocalization. This revealed an overlapping distribution of EphA2 and E-cadherin along the lateral membranes of epithelial cells and, specifically, within sites of cell—cell contact. Vertical sectioning by confocal microscopy confirmed colocalization of E-cadherin and EphA2 within sites of cell—cell contact.

To test whether the colocalization of EphA2 and E-cadherin indicated a functional link between the two proteins, calcium-dependent E-cadherin-mediated adhesion was disrupted by supplementing the cell culture medium with 4 mm EGTA, a calcium-chelating agent. Stable cell—cell contacts in monolayers of MCF-10A cells were disrupted by the addition of EGTA (4 mM, 30 min, 37° C.) to the culture medium. After removal of the EGTA, normal growth medium was returned for 0–120 min. EphA2 was immunoprecipitated and Western blot analysis performed with phosphotyrosine-specific (PY20) antibodies. The blot was stripped and reprobed with EphA2 antibodies as a loading control. Staining with EphA2-specific antibodies assessed changes in the subcellular distribution of EphA2 before and after restoration of cell—cell adhesions. EGTA treatment caused EphA2 dephosphorylation and induced either a diffuse or membrane ruffle pattern of staining, which was reminiscent of EphA2 in metastatic cells. Subsequent restoration of normal levels of extracellular calcium restored normal levels of EphA2 phosphorylation and cell—cell localization within 5 min.

Although results with EGTA-treated samples implicate cell—cell adhesion with the control of EphA2 phosphorylation and subcellular localization, E-cadherin was further tested to determine whether it contributed to this regulation. Following treatment of MCF-10A cell monolayers with EGTA, normal medium conditions were restored in the absence or presence of function-blocking E-cadherin antibodies or peptides. Isotype control antibodies and scrambled peptides were included as matched negative controls. Immunoprecipitated EphA2 was subjected to Western blot analysis with phosphotyrosine (PY20) antibodies. The same blot was stripped and reprobed with EphA2 antibodies as a loading control. EphA2 localization was determined after calcium restoration in the absence or presence of E-cadherin inhibitors. The cell culture medium was supplemented with function-blocking E-cadherin antibodies and peptides (DEMA-1 antibodies or HAV peptides (Vestweber, D. et al. Rabbit antiserum against a purified surface glycoprotein decompacts mouse preimplantation embryos and reacts with specific adult tissues. Exp. Cell Res., 152: 169–178, 1984; Ozawa, M., et al. A possible new adhesive site in the cell-adhesion molecule uvomorulin. Mech. Dev., 33: 49–56. 1990). When inhibitors of E-cadherin function were added to the medium concomitant with the restoration of extracellular calcium, EphA2 did not become tyrosine-phosphorylated and remained diffuse or present within membrane ruffles. In contrast, isotype-matched control antibodies and scrambled pepticles did not prevent EphA2 phosphorylation or localization within intercellular junctions. Specific inhibition of E-cadherin with these inhibitors also blocked EphA2 phosphorylation and cell—cell localization upon treatment of confluent cell monolayers, thus confirming that EphA2 phosphorylation and localization are sensitive to the functioning of E-cadherin.

Both Eph family receptor tyrosine kinases and their ephrin ligands are bound to the cell surface (van der Geer, P., et al. Receptor protein tyrosine kinases and their signal transduction pathways. Annu. Rev. Cell Biol., 10., 251–337. 1994; Gale. N. W., et al. Ephrins and their receptors: a repulsive topic? Cell Tissue Res., 290: 227–241, 1997), so cells must be in close contact to facilitate Eph-ephrin interactions. Little is known, however, about the nature of these contacts and their precise effects on Ephephrin interactions.

Because many breast tumors lack E-cadherin and have unstable cell—cell junctions (Behrens. J., et al. Cell—cell adhesion in invasion and metastasis of carcinomas. Cancer Treat. Res., 71: 251–266, 1994; Bale. S. N., Molecular and cellular analysis of basement membrane Invasion by human breast cancer cells in Matrigal-based in vitro assays. Breast Cancer Res. Treat, 24: 241–255, 1993), expression of E-cadherin and its effects on EphA2 phosphorylation in mammary epithelial cells was tested. E-cadherin function was inhibited either by removal of $Ca^{2+}$or with function-blocking antibodies or peptides reduced EphA2 phosphorylation and caused EphA2 to redistribute into membrane ruffles. Conversely, expression of E-cadherin in MDA-MB-231 cells restored EphA2 phosphorylation and localization to sites of cell—cell contact. The simplest explanation for these results is that E-cadherin stabilizes cell—cell contacts and, thereby, facilitates interactions between EphA2 and its ligands.

E-cadherin and EphA2 are expressed in overlapping patterns, but co-immunoprecipitation of EphA2 and E-cadherin has not been attained and EphA2 does not cocluster with E-cadherin at the cell surface in response to antibody-mediated aggregation of either molecule. Experimental conditions used for protein extraction may dissociate such interactions or a small fraction of activated EphA2 may cocluster with E-cadherin. Direct interaction between the two molecules may not be necessary if E-cadherin primarily serves to stabilize cell—cell contacts and thereby promote interactions between EphA2 and its ligands. Other aspects of E-cadherin function, such as signaling (Kinch. M. S., et al. E-cadherin engagement stimulates tyrosine phosphorylation. Cell Adhes. Commun., 4: 425–437,1997), cytoskeletal association (Vestweber, D., et al. Some structural and functional aspects of the cell adhesion molecule uvomorulin. Cell Differ. 15: 269–273, 1984), and junction formation (Geiger, B., et al. Annu. Rev. Cell Biol., 8: 307–332, 1992) might also target EphA2 to sites of cell—cell contact.

EphA2 is Responsive to E-Cadherin Expression in Metastatic Cells

To examine further the link between EphA2 and E-cadherin, MDA-MB-231 cells were transfected with E-cadherin and selected for levels of E-cadherin expression that were equivalent to MCF-10A cells. The subcellular distribution of EphA2 and paxillin was assessed by immunofluorescence microscopy in control and E-cadherin transfected MDA-MB-231 cells. E-cadherin promoted a redistribution of EphA2 into cell—cell contacts and decreased focal adhesions. As controls, cells were transfected with empty vector. EphA2 in 231-neo was not phosphorylated and was enriched within membrane ruffles. In contrast, the EphA2 in E-cadherin transfected cells redistributed into sites of cell—cell contacts and had levels of phosphotyrosine that were comparable with that of MCF-10A cells. When the phosphotyrosine content of immunoprecipitated EphA2 was measured by Western blot analysis following transfection of MDA-MB-231 cells with E-cadherin or a matched vector control. MCF-10A was included as a positive control for EphA2 tyrosine phosphorylation. The blot was stripped and reprobed with EphA2-specific antibodies; as a loading control. These changes in EphA2 phosphorylation and localization increased with cell density, consistent with an idea that E-cadherin function regulates EphA2 phosphorylation and localization.

EphA2 Regulates Cell Adhesion and Proliferation

Microscopic analysis performed as described above revealed that E-cadherin expression altered the adhesive profile of MDA-MB-231 cells. Whereas parental and empty vector cells were mesenchymal in appearance and readily grew atop one another, the E-cadherin-transfected cells had more prominent cell—cell adhesions and grew as single-cell monolayers. Analysis of cell-ECM[3] attachments by staining with paxillin-specific antibodies revealed numerous focal adhesions in control MDA-MB-231 cells, whereas E-cadherin transfected cells had fewer focal adhesions. The decrease in focal adhesions was most prominent in whereas E-cadherin transfected cells within colonies, whereas individual calls had focal adhesions that were comparable with controls.

EphA2 activation contributes to the decreased cell-ECM adhesion. To activate EphA2 in MDA-MB-231 cells, EphA2 was aggregated at the cell surface with specific antibodies (as described above), which caused a rapid loss of focal adhesions within 5 min. This was confirmed by paxillin staining and by interference reflection microscopy. Specifically, the presence of focal adhesions was assessed by immunostaining for paxillin in MDA-MB-231 cells before and after activation of EphA2 by antibody-mediated aggregation. The incubation of cells with either primary or secondary antibodies alone did not alter the presence of focal adhesions, whereas EphA2 aggregation dissipated focal adhesions. Similar results were obtained in other neoplastic cell lines. In contrast, treatment with either primary or secondary antibodies alone did not alter focal adhesions.

Focal adhesions are sites of intracellular signaling that promote cell growth (Burridge, K., et al. Focal adhesions, contractility, and signaling. Annu. Rev. Cell Dev. Biol., 12: 463–518. 1996; Burridge, K., et al. Focal adhesions, contractility, and signaling. Annu. Rev. Cell Dev. Biol., 12: 463–518. 1996). Because EphA2 activation blocks focal adhesions, the impact of EphA2 activation on cell growth was assessed. EphA2 was activated with specific antibodies or B61-IgG ligand-bodies (as described above). Concomitant with receptor cross-linking, BrdUrd was included in the culture medium and DNA synthesis was measured over the following 4 h. As shown in Table I, EphA2 activation decreased the proliferation in MDA-MB-231 cells (31% reduction; $P<0.001$), whereas control conditions (primary or secondary antibodies alone and isotype controls) did not change cell growth. The short duration of EphA2 signaling that is induced by antibody aggregation likely underestimates EphA2's growth-inhibitory potential. A similar decrease in cell growth was obtained following EphA2 activation in other cell types, including MDA-MB-435 cells (22% reduction; $P<0.0005$) and MCF-10A cells (16% reduction; $P<0.01$). For experiments with MCF-10A, cells were plated at low cell density and individual cells were scored (to preclude cell—cell contacts that might otherwise activate EphA2).

TABLE I

EphA2 Activation Inhibits Cell Proliferation[a]

| Cell Line | Treatment | % BrdUrd uptake (mean ± SE) | Statistical analysis[b] |
| --- | --- | --- | --- |
| MDA-MB-231 | Untreated | 43.8 ± 2.0 | |
| | Primary Ab[c] alone | 44.1 ± 2.2 | >0.43 |
| | Secondary Ab alone | 39.7 ± 2.3 | >0.21 |
| | Primary + secondary | 30.4 ± 1.7 | <0.0001 |
| | Control-IgG + secondary | 43.0 ± 2.1 | >0.44 |
| | B61-IgG + secondary | 29.1 ± 3.1 | <0.01[d] |
| MDA-MB-435 | Untreated | 52.8 ± 5.1 | |
| | Primary Ab alone | 52.6 ± 3.4 | >0.25 |
| | Secondary Ab alone | 52.8 ± 6.3 | >0.39 |
| | Primary + secondary | 39.6 ± 0 | |
| | Untreated | 53.6 ± 1.5 | >0.43 |
| MCF-10A (low density) | Primary Ab alone | 53.9 ± 0.8 | <0.00005 |
| | Secondary Ab alone | 55.1 ± 0-5 | >0.22 |
| | Primary + secondary | 45.0 ± 1.4 | <0.01 |

[a]BrdUrd uptake into newly synthesized DNA was measured for 4 h after cross-linking of EphA2 at the cell surface with specific antibodies. The data represent at least three independent, double-blinded experiments. Cell growth was determined in at least 100 cells from each experimental and control, and the results shown are compared with DNA synthesis with untreated (untreate4 samples. None of the differences between or among individual negative controls (untreated, primary antibody alone, or secondary antibody alone) were significant ($P > 0.05$).
[b]Statistical analyses compared the experimental to untreated for each sample.
[c]Ab. antibody.
[d]For the fusion proteins, there was also a significant difference ($P < 0.02$) between the control and B61 fusion proteins.

An immediate consequence of EphA2 activation is decreased cell-ECM contact at focal adhesions. Focal adhesions are sites of membrane-cytoskeletal interaction that provide anchorage for cell migration and invasion (Burridge, K, et al. Focal adhesions: transmembrane junctions between the extracellular matrix and the cytoskeleton. Annu. Rev. Cell Biol., 4: 487–525. 1988). Focal adhesions also play critical roles in signal transduction, where they organize intracellular signals that control cell growth and survival (Burridge, K, et al. Focal adhesions: transmembrane junctions between the extracellular matrix and the cytoskeleton. Annu. Rev. Cell Biol., 4: 487–525. 1988; Parsons, J. T. Integrin-mediated signaling: regulation by protein tyrosine kinases and small GTP-binding proteins. Curr. Opin. Cell Biol. 8: 146–152, 1996). E-cadherin-mediated stabilization of ligand binding may induce EphA2 to block focal adhesions. Consistent with this, it is understood that epithelial cells balance their cell—cell and cell-ECM adhesions and that this is linked with the proper functioning of E-cadherin (Kinch, M. S., et al. Altered adhesions in ras-transformed breast epitheilal cells. Biochern. Soc. Trans. 23: 446–450, 1995; Vestweber, D. et al. Identification of a putative cell adhesion domain of uvomorulin. EMBO J., 4: 3393–3398, 1985). Individual epithelial cells have more focal adhesions than cells within colonies, whereas cells with decreased E-cadherin function have increased cell-matrix adhesion, regardless of cell density (Kinch, et al., 1995). Many proteins that interact with Eph kinases regulate cell adhesion or cytoskeletal organization, including the p85 subunit of phosphatidylinositol 3'-kinase, Src, Fyn, and Ras-GAP (Pandy, et al., 1994; Stein, E., et al. Nck recruitment to Eph receptor, EphB1/ELK couples ligand activation to c-Jun kinase. J. Biol. Chem. 273: 1303–1308, 1998; Stein, E., et al. Eph receptors discriminate specific ligand ollgomers to determine alternative signaling complexes, attachment, and assembly responses. Genes Dev., 12: 667–678. 1988): Zisch, A., et al. Complex formation between EphB2 and Src requires phosphorylation of tyrosine 611 in the EphB2 juxtamembrane region. Oncogene, 16: 2657–2670. 1998).

Focal adhesions initiate signals that promote cell growth, and it follows that loss of these structures may contribute to decreased cell growth following EphA2 activation. Loss of EphA2 activation might contribute to deregulated growth of neoplastic cells by increasing signals from focal adhesions. This would be consistent with evidence that neoplastic cells have increased signaling by focal adhesion proteins (e.g., FAK; Owens, L V., et al. Overexpression of the focal adhesion kinase (p125FAK) in invasive human tumors. Cancer Res. 55: 2752–2755, 1995). Although EphA2 activation decreases cell growth, the expression pattern of EphA2 does not fit the classic pattern of a tumor suppressor. Most tumor suppressors are inactivated either because of decreased expression or loss of enzymatic activity. In contrast, neoplastic cells express high levels of EphA2, which, although non-phosphorylated, retains comparable levels of enzymatic activity. An alternative explanation is that EphA2 positively regulates cell growth but that this signaling is reduced in nontransformed epithelia. Support for this includes evidence that EphA2 is overexpressed in neoplastic cells and is supported by the fact that other Eph kinases (e.g., EphA1) are oncogenic (Maru, Y., et al. Overexpression confers an oncogenic potential upon the eph gene. Oncogene, 5: 445–447, 1990). In this scenario, EphA2 "activation" by E-cadherin or receptor aggregation might decrease EphA2 function, perhaps by reducing EphA2 expression levels. It is intriguing that the lowest levels of EphA2 are found in cells where it is phosphorylated and that ligand-mediated aggregation decreases EphA2 expression levels. A third possibility is that EphA2 functions very differently in normal and neoplastic epithelia. The phosphotyrosine content and subcellular localization of EphA2 differ in normal and neoplastic cells, and either property could alter substrate specificity or availability. Indeed, tyrosine-phosphorylated EphA2 (but not unphosphorylated EphA2) interacts with the phosphatidylinositol 3'-kinase and the SLAP adapter protein (Pandey, A., et al. Characterization of a novel Src-like adapter protein that associates with the Eck receptor tyroosine kinase. J. Biol. Chem., 270: 19201–19204, 1995). SLAP was recently shown to negatively regulate cell growth (Pandey, A., et al. 1995), which is supportive of our evidence that EphA2 also regulated cell proliferation.

Example 2

EphA2 Overexpression Causes Tumorigenesis and Metastasis of Mammary Epithelial Cells Elevated levels of protein tyrosine phosphorylation contribute to a malignant phenotype, although the kinases that are responsible for this signaling remain largely unknown. This example shows increased levels of the EphA2 protein tyrosine kinase were present in cell models and clinical specimens of breast cancer. EphA2 overexpression was sufficient to confer malignant transformation and metastatic potential upon non-transformed (MCF-10A) mammary epithelial cells. The transforming capacity of EphA2 was related to its ability to control cellular adhesions and with the failure of EphA2 to interact with its cell-attached ligands. Interestingly, stimulation of EphA2 was sufficient to reverse the malignant growth and invasiveness of EphA2-transformed cells. Altogether, these results identified EphA2 as a powerful oncoprotein in breast cancer.

Cells and Antibodies

All cells were cultured as described previously (Zantek, N. D., et al. E-cadherin regulates the function of the EphA2 receptor tyrosine kinase. Cell Growth & Differentiation, 10: 629–638, 1999). Antibodies specific for β-catenin and phosphotyrosine (PY-20) were purchased ftorn Transduction Laboratories (Lexington, Ky.). Antibodies specific for phosphotyrosine (4G10) and EphA2 were purchased from Upstate Biologicals, Inc. (Lake Placid, N.Y.). EphrinA I-$F_c$ was a generous gift from Dr. B. Wang (Case Western Reserve).

Western Blot Analysis and Immunoprecipitation

Western blot analyses were performed as described previously (Zantek, N. D., et al., 1999) and antibody binding was detected by enhanced chemiluminescence (Pierce) and autoradiography (Kodak X-OMAT; Rochester, N.Y.). To confirm equal sample loading, the blots were stripped and reprobed with antibodies specific for β-catenin or vinculin.

Immunohistochemistry and Immunofluorescence Staining

Formalin-fixed, paraffin embedded "sausage" slides, each containing 15–30 breast cancer specimens, were kindly provided by B. J. Kerns (BioGenex) and stained and scored as described (Walker-Daniels, J. et al. Pverexpression of the EphA2 tyrosine kinase in prostate cancer. Prostate 41:275–280, 1999). Mean immunostaining intensity in benign and malignant breast were compared using Student's t-test with statistical software (SAS for Windows ver. 6.04 and Microsoft Excel '97), defining $P<0.05$ as significant. Staining of cell monolayers with EphA2 antibodies (clones D7 or 132136) was performed as described previously (Zantek, N. D., et al., 1999).

Transfection and Selection

Monolayers of MCF-10A cells were co-transfected with the pNeoMSV-EphA2 (generously provided by Dr. T. Hunter, Scripps) and pBABE-Puro eukaryotic expression vectors, at a 4:1 ratio, using Lipofectamine Plus (GIBCO; Grand Island, N.Y.). As a control for the transfection procedure, a parallel transfection was performed using pNeoMSV and pBABE-Puro. Puromycin-resistant cells were selected by supplementing the growth medium with 1 μg/mL puromycin (Sigma, St. Louis, Mo.). EphA2 overexpression was confirmed by Western blot analysis with specific antibodies. All experiments were performed using bulk culture transfectants and identical results were obtained using cells from two separate transfections with EphA2 cDNAs. Parental cells and cultures transfected with pBABE-Puro were used as negative controls.

Cell Adhesion Assays

Monolayers of MCF-I OA cells transfected with empty vector or EphA2 were suspended using 4.5 mM EDTA. Cell-cell aggregation assays were performed by suspending $3\times10^5$ cells/ml, in media for 30 min. at 37° C. and 5% $CO_2$. The average size of cell colonies was determined using light microscopy by dividing the total number of cells in each field by the number of particles (clusters containing one or more cells). To measure cell-ECM attachments, $5\times10$ suspended cells were plated into a 35 min tissue culture dish for 30 minutes at 37° C. Weakly adherent cells were detached by three vigorous washes and the remaining adherent cells were suspended with trypsin and counted using a hemacytometer. The average number of attached cells from at least four separate experiments is reported.

Colony Formation in Soft Agar

Colony formation in soft agar was performed as described (Clark, G. J., et al. Overexpression of the Ras-related TC21/R-Ras2 protein may contribute to the development of human breast cancers. Oncogene, 12: 169–176, 1996). Colony formation was scored microscopically, defining clusters of at least three cells as a positive. For experiments with EphrinA I-$F_c$, 0.5 μg/mL of EphrinA1-$F_c$ or a matched vehicle (50% Glycerol in PBS) was included in top agar solution and ligand was replenished daily with fresh media.

Cell Behavior in Matrigel

The behavior of cells in Matrigel was performed as described previously (Giunciuglio, D., et al. Invasive phenotype of MCF-10A cells overexpressing c-Ha-ras and c-erbB-2 oncogenes. Intl J Cancer, 63: 815–822, 1995). Briefly, tissue culture dishes were coated with Matrigel (Collaborative, Bedford, NIA) at 37° C. before adding $1 \times 10^5$ vector or EphA2 transfected MCF-10A cells. The behavior of EphA2-overexpressing cells was assessed at 6 hour intervals using an inverted light microscope (Olympus IX-70). For experiments with EphrinA $I-F_c$, the culture medium was supplemented with 0.5 μg/mL of EphrinA1-$F_c$ or an appropriately matched vehicle control. All images were recorded onto 35 mm film (Kodak T-Max-400).

Xenograft Analyses

Three to four week-old athymic (nu/nu) mice were purchased from Harlan Sprague Dawley (Indianapolis, Ind.) and Charles River (Wilmington, Mass.) and acclimated for 7–10 days. For subcutaneous implantation, $1 \times 10^6$ or $5 \times 10^6$ vector or EphA2 transfected MCF-10A cells were suspended in 100 μL of fresh media and innoculated into the right craniolateral thorax (axilla) using a 23-gauge needle. For tail vein injections, $1 \times 10^6$ cells were injected into the tail vein and mice were monitored for 7–28 days. At necropsy, primary tumors and all organs were evaluated macroscopically for the presence of tumors. Tissue samples of the primary tumor and organs were fixed in 10% buffered neutral formalin and embedded in paraffin. Tissue sections of the tumors and lung were stained with hematoxylin and eosin to assess morphology. Lung sections were stained with cytokeratin (AE1/AE3) or thrombin-specific antibodies (DAKO, Carpinteria, Calif.) to confirm the epithelial nature of lung metastases.

Elevated EphA2 Protein Levels in Cancer Cells

To compare the levels of EphA2 protein in cell models of non-transformed (MCF-10A, M MCF-12A, MCF-10-2) and aggressive (Hs578T, MDA-436, MDA-435, MDA-231, BT549) breast epithelia (Pauley, R. J., et al. The MCF 10 family of spontaneously immortalized human breast epithelial cell lines: models of neoplastic progression. Eur J Cancer Prev, 2 Suppl 3: 67–76, 1993; Bae, S. N., et al. Molecular and cellular analysis of basement membrane invasion by human breast cancer cells in Matrigel-based in vitro assays. Breast Cancer Res Treat, 24: 241–255, 1993), equal amounts of whole cell extracts were resolved by SDS-PAGE and subjected to Western blot analysis using EphA2-specific antibodies. Whole cell lysates from cell models of non-transformed mammary epithelia or aggressive breast cancers were resolved by SDS-PAGE and Western blot analysis was performed using EphA2-specific (D7) antibodies. As a loading control, the membranes were stripped and reprobed with antibodies specific for β-catenin. EphA2 protein levels were assessed by immunohistochernical staining of formalin-fixed, paraffinembedded specimens of benign or malignant breast specimens (see Table II for details and data analysis). The non-immunoreactive cytoplasm of benign epithelium contrasts with the strong and diffuse immunoreactivity of malignant cells. Whereas lower levels of EphA2 protein were detected in non-transformed epithelial cells, more EphA2 was detected in aggressive carcinoma cells. Identical results were obtained when equivalent numbers of cells or equal amounts of protein were analyzed. Increased levels of EphA2 in aggressive cell models were also confirmed using different EphA2 antibodies (D7, B2D6, EK166B), revealing that the differences in EphA2 levels did not reflect changes in a single epitope. The blots were stripped and re-probed with antibodies specific for β-catenin or vinculin, which confirmed equal sample loading.

Because of the elevated levels of EphA2 in cell models, EphA2 was measured in clinical specimens of breast cancer. Immunohistochemical staining of formalin-fixed, paraffin-embedded tissue sections revealed a low level of EphA2 immunoreactivity in benign mammary epithelia, with an average staining intensity of 0.1 (using a 0–3 scale to report staining intensity; Table II). EphA2 immunoreactivity was increased in breast carcinoma specimens, with an average staining intensity of 2.9. Increased staining intensity was accompanied by a larger percentage of carcinoma cells (an average of 87%) that stained positive for EphA2 as compared with benign mammary epithelial cells (an average of 3%). The data suggest that the EphA tyrosine kinase was overexpressed in many clinical specimens and cell models of breast cancer, where it functions as a powerful oncoprotein.

Consistent results with several cell models suggest that elevated levels of EphA2 are highly relevant to breast cancer. High levels of EphA2 are found in clinical specimens and aggressive cell models of breast cancer; Recent studies reveal that EphA2 overexpression may similarly apply to advanced melanoma (Easty, D. J., et al. Abnormal protein tyrosine kinase gene expression during melanoma progression and metastasis. Intl J Cancer, 60: 129–136, 1995), colon cancer (Rosenberg, I. M., et al., Epithelial cell kinase-B61: an autocrine loop modulating intestinal epithelial migration and barrier function. Am J Physiol, 273: G824-G8321997) and prostate cancer (Walker-Daniels, J., et al., 1999). The fact that elevated EphA2 levels are found on multiple types of cancer suggests that EphA2 overexpression is a common event in the metastatic progression of carcinoma cells.

TABLE II

EphA2 Immunoreactivity in Breast Cancer Specimens

| | EphA2 Staining Intensity | | | |
|---|---|---|---|---|
| | 0 (Negative) | 1 (Weak) | 2 (Moderate) | 3 (Strong) |
| Benign Breast | | | | |
| Sample Number | 9 | 3 | 0 | 0 |
| % Cells Positive | <5% | 10–20% | | |
| Breast Carcinoma | | | | |
| Sample Number | 1 | 0 | 6 | 5 |
| % Cells Positive | <5% | | 50–100% | 90–100% |

Table II. Formalin-fixed, paraffin-embedded specimens of benign and malignant mammary tissues were stained with EphA2 antibodies and evaluated. Statistical analyses revealed differences in EphA2 staining of benign and malignant samples ($P < 1 \times 10^{-6}$).

In a related study, EphA2 protein levels were measured in non-transformed, tumorigenic, or metastatic mammary, prostate epitelial cells, and lung cancer cells by Western blot analysis of whole cell lysates. The highest levels of EphA2 consistently were found in cells with the greatest metastatic potential. The EphA2 in non-transformed epitelia was primarily found in cell—cell contacts, where interaction with its membrane-anchored ligands caused it to be tyrosine phosphoylated. In metastatic cells, EphA2 is diffusely distributed and is not tyrosine phosphorylated. EphA2 staining of clinical specimens of breast and prostate cancer was measured by immunohistochemical staining of clinical specimens. See Table III. The specimens were counterstained with hemotoxylin to visualize tissue organization.

TABLE III

| | EphA2 Staining Intensity | | | |
|---|---|---|---|---|
| | 0 (Negative) | 1 (Weak) | 2 (Moderate) | 3 (Strong) |
| Benign Breast | | | | |
| Sample Number | 9 | 3 | 0 | 0 |
| % Cells Positive | <5% | 10–20% | | |
| Breast Carcinoma | | | | |
| Sample Number | 1 | 0 | 6 | 5 |
| % Cells Positive | <5% | | 50–100% | 90–100% |
| Benign Prostate | | | | |
| Sample Number | 5 | 1 | 0 | 0 |
| % Cells Positive | <5% | 10% | | |
| Prostatic Carcinoma | | | | |
| Sample Number | 0 | 1 | 9 | 5 |
| % Cells Positive | 40% | 60–100% | 90–100% | |
| Lung Carcinoma (Stage 1) | | | | |
| Sample Number | 6 | 49 | 65 | 18 |

EphA2 Overexpression Alters Cellular Adhesion

To assess the consequences of EphA2 overexpression, MCF-10A cells were transfected with human EphA2 cDNA or a vector control. MCF-10A cells were co-transfected with pBabe-puro and either pNeoMSV or pNeoMSV-EphA2. Western blot analysis of whole cell lysates, resolved by SDS-PAGE, was performed using EphA2-specific antibodies. The membranes were stripped and reprobed with -cantenin antibodies as a control for sample loading. The phosphotyrosine content of EphA2 was determined by Western blot analysis of immunoprecipitated EphA2. The blots were then stripped and reprobed with EphA2-specific antibodies (clone D7).

The morphology of vector and EphA2-transfected cells was assessed by phase-contrast microscopy. Whereas control cells organize into colonies, EphA2-overexpressing cells resist interactions with one-another. Monolayers of vector or EphA2-transfected MCF-10A cells were stained with EphA2-specific antibodies. EphA2 was enriched within sites of cell—cell contact in vector-transfected controls buy was diffusely distributed in EphA2-transfected cells. Assays of ECM attachments (left graph of FIG. 1) were performed by incubating cells onto purified ECM for 30 min. at 37 C. The fraction of cells that remained adherent after vigorous washing is shown in FIG. 1. Rosette assays measured the average size of cell—cell aggregates in suspension (right graph). Asterisks denote that EphA2 overexpressing cells had statisically significant increases in ECM contacts ($P<4\times10^{-4}$) and decreased cell—cell ($P<3\times10^{-5}$). Thus, after establishing cultures of MCF-10A cells with stable overexpression of EphA2, microscopic evaluation revealed differences in the cell morphology as compared to vector-transfected control cells. Non-transformed MCF-10A cells displayed an epithelial morphology and interacted with one-another, even at low cell density. In contrast, EphA2-overexpressing MCF-10A cells ($MCF^{EphA2}$) adopted a fibroblast-like morphology and did not form cell—cell contacts, even at high cell density. To confirm that the mesenchymal morphology did not represent clonal variation, a separate sample of MCF-10A cells was transfected with EphA2 cDNAs and yielded identical results.

EphA2 overexpression reorganizes cellular adhesions and prevents ligand-mediated stimulation of EphA2. However, restoration of ligand binding reverses the malignant phenotype of EphA2-overexpressing cells.

EphA2 Overexpression Decreases its Phosphotyrosine Content

Since stable cell—cell contacts cause EphA2 to become enriched within sites of cell—cell contact (Zantek, N. D., et al., 1999) EphA2 subcellular localization was assessed by immunostaining with specific antibodies as described above. The EphA2 on non-transformed MCF-10A cells was restricted to a narrow line where adjacent cells came into direct contact, with little staining of membrane that was not in contact with neighboring cells. In contrast, the pattern of EphA2 staining on $MCF^{EphA2}$ cells was diffiase, with little staining of cell—cell contacts.

The lack of EphA2 within cell—cell contacts in $MCF^{EphA2}$ cells was intriguing since EphA2 is stimulated by ligands that are anchored to the cell membrane (Bartley, T. D., et al., BA B61 is a ligand for the ECK receptor protein-tyrosine kinase. Nature, 368: 558–560, 1994). To measure EphA2 stimulation, the phosphotyrosine content of immunoprecipitated EphA2 was measured by Western blot analysis with phosphotyrosine specific antibodies. Whereas the EphA2 in vector-transfected MCF-10A cells was tyrosine phosphorylated, EphA2 was not tyrosine phosphorylated in $MCF^{EphA2}$ cells. The decreased phosphotyrosine content was confirmed using multiple EphA2 antibodies for immunoprecipitation (D7, B2D6) and different phosphotyrosine-specific antibodies (4G 10, PY20) for Western blot analyses.

To test if the EphA2 on $MCF^{EphA2}$ cells could be stimulated by an exogenous ligand, EphrinA I-$F_c$, which consists of the extracellular domain of ephrinA1 linked to immunoglobulin heavy chain, was used (16). Treatment of MCF EphA2 cells with 0.5 μg/mL EphrinA1-Fc increased the phosphotyrosine content of EphA2. Despite its inability to interact with its endogenous ligands, the EphA2 in $MCF^{EphA2}$ cells could respond to exogenous stimuli.

EphA2 Overexpression Causes Malignant Transformation

The pattern of defects in cell adhesion, EphA2 subcellular distribution and phosphotyrosine content in $MCF^{EphA2}$ cells were all reminiscent of metastatic cells (Zantek, N. D., et al., 1999), which suggested that EphA2 overexpression induced malignant transformation. To test this theory, $MCF^{EphA2}$ cells were treated with 0.5 μg/mL EphrinA1-$F_c$ (EA1-$F_c$ for 8 minutes before immunoprecipitation of EphA2 with specific antibodies (clone D7). Western blot analysis with phosphotyrosine specific antibodies (PY20 and 4G10) revealed that EphrinA1-$F_c$ increased the phosphotyrosine content of EphA2. To measure anchorage-independent cell growth and survival, $1\times10^4$ vector or EphA2-transfected MCF-10A cells were suspended in soft agar ±0.5 μg/ml, EphrinA1-$F_c$ (Ea1-$F_c$). After seven days, colony formation was scored microscopically, defining clusters containing at least three cells as a positive colony. $MCF^{EphA2}$ cells demonstrated significant increases in anchorage independent growth ($P<4\times10^{-7}$) whereas EphrinA1-$F_c$ treatment significantly blocks the growth (by about 49%) of MCF EphA2 cells ($P<5\times10^6$). The phenotype of control and EphA2-transformed MCF-10A cells was determined after incubation atop polymerized Matrigel ±0.5 μg/mL EphrinA1-$F_c$ or an appropriately matched vehicle. Whereas control MCF-10A cells organized into spherical colonies, $MCF^{EphA2}$ cells displayed a stellate growth pattern in Matrigel that mimicked the behavior of aggressive breast cancer cells (MDA-MB-231). Notably, treatment with 0.5 μg/ml EphrinA1-$F_c$ caused the phenotype of MCF$^{EphA2}$ cells to be indistinguishable from control MCF-10A cells. Thus, EphA2 stimulation reversed the effects of EphA2 overexpression.

Based on evidence linking the aggressiveness of tumor cells in vivo with their behavior in Matrigel (17)(13), vector and EphA2 overexpressing MCF-10A cells were allowed to interact with Matrigel. Non-transformed MCF-10A cells rapidly organized into spherical colonies when cultured on Matrigel whereas MCF$^{EhA2}$ cells adopted a stellate organization that was indistinguishable from the behavior of metastatic cells (e.g., MDA-MB-231, MDA-MB,435). To test if EphA2 stimulation could alter cell behavior on Matrigel, the MCF EphA2 cells were treated with 0.5 µg/mL EphrinA 1-F$_c$, which restored a spherical phenotype that was comparable to nontransformed MCF-10A cells.

EphA2 Overexpression Confers Tumorigenic and Metastatic Potential

Since in vitro analyses of transformation do not always predict tumorigenic potential in vivo, control or EphA2-overexpressing MCF-10A cells were implanted into athymic (nu/nu) mice. MCF$^{EphA2}$ cells were implanted subcutaneously into the right craniolateral thorax (axilla) of athymic (nu/nu) mice. Within four days, the implanted cells formed palpable masses in 19 out of 19 mice. The histologic appearance of the tumor revealed that these masses were almost entirely composed of moderately differentiated and invasive tumor cells that formed dysplastic tubules with fluid-filled lumens. Neoplastic cells invaded adjacent skeletal muscle fibers. MCF$^{FPA2}$ inoculated intravenously into the tail vein of athymic mice colonized the lung and were enriched within large vesicles. Histologic appearance of pulmonary tumor thrombi in athymic mice revealed that tumor cells partially to totally obstructed intravascular spaces but did not invade the vessel wall. See Table IV for details and data analysis.

Specifically, the median volume of resulting tumors related to the number of implanted cells and reached an average of 300 mm$^3$ (for samples injected with 5×10$^6$ cells) within 10 days (Table IV). Necropsy revealed that the tumors were firmly attached to the underlying axillary muscle and surrounded by fibrous tissue. Histologically, the neoplastic cells were invasive and associated with fibrous connective tissue. These neoplastic cells exhibited moderate cytoplasmic and nuclear pleiomorphism and formed dysplastic tubular and secreting structures. In control experiments, cells transfected with vector DNA failed to grow in athymic mice (0 of 13; Table IV) and necropsy failed to identify any growth or invasion of these cells.

Since the highest levels of EphA2 were consistently found in breast cancer cells that are metastatic in vivo (Bae, S. N. et al., 1993), 1×10$^6$ control or MCF cells were injected into the tail vein of athymic mice. Within seven days, necropsy revealed lung micrometastases within large vessels in 2 of 4 mice injected with MCF$^{EphA2}$ cells (Table IV. The metastases were generally found to occlude large blood vessels but did not breach the vessel wall. Immunohistochemical staining with cytokeratin antibodies confirmed the epithelial nature of the thrombus and a lack of anti-thrombin staining revealed that the thrombus did not represent an abnormal or atypical outgrowth of endothelial cells. No lung colonization was observed in mice that had been injected with control MCF-10A cells (Table IV).

TABLE IV

Tumorigenic and Metastatic Potential of EphA2-Transformed MCF-10A Cells

| Cell | Site of Inoculation | # of Cells Injected | Incidence of Tumorigenicity | Tumor Volume (mm$^3$) |
|---|---|---|---|---|
| Ctrl | Subcutaneous | 1 × 10$^6$ | 0/9 | NA |
| EphA2 | | 1 × 10$^6$ | 9/9 | 66 ± 20 |
| Ctrl | Subcutaneous | 5 × 10$^6$ | 0/4 | NA |
| EphA2 | | 5 × 10$^6$ | 10/10 | 293 ± 70 |
| Ctrl | Tail Vein | 1 × 10$^6$ | 0/4 | |
| EphA2 | | 1 × 10$^6$ | 2/4 | |

Table IV. Tumorigenesis by MCF-10 A cells (±EphA2) was evaluated following subcutaneous or tail vein injection. The significance of tumor formation was estimated to be $P<1.3\times 10^{-7}$ as determined by $\chi^2$ analyses.

These results provide the first evidence that EphA2 is not merely a marker, but an active participant in tumorigenesis and metastasis. EphA2-overexpressing MCF-10A cells displayed the hallmarks of malignant transformation as defined in vitro and in vivo. MCF$^{EphA2}$ cells formed tumors in vivo at a high frequency, which is remarkable given that other oncogenes (e.g., Ras, HER2, TC21) are insufficient to convey tumorigenic or metastatic potential upon MCF-10A cells (Giunciuglio, D., et al., 1995)(Clark, G. J., et al. 1996). Thus, that EphA2 overexpression may be particularly relevant to metastatic progression.

EphA2 overexpression causes defects in cell adhesion that are characteristic of aggressive cancer cells. The weakened cell—cell contacts and increased ECM adhesions of MCF$^{EphA2}$ cells resemble the adhesive phenotype of oncogene-transformed and tumor-derived epithelial cells (Kinch, M. S., et al. Tyrosine phosphorylation regulates the adhesions of ras-transformed breast epithelia. J Cell Biol, 130: 461–471, 1995). Consistent with this, the highest levels of EphA2 are consistently found on tumor-derived cell lines that display weak cell—cell contacts and increased ECM invasiveness (Bae, S. N., et al., 1993). One possible explanation is that EphA2 phosphorylates adhesion or cytoskeletal proteins to alter the balance between cell—cell and ECM adhesions. This idea is supported by evidence linking EphA2 to adhesion and cytoskeletal proteins, including E-cadherin FAK, SLAP and PI 3-kinase (Miao, H., et al. EphA2 kinase associates with focal adhesion kinase and upon activation, inhibits integrin-mediated cell adhesion and migration. Nature Cell Biol, 2: 62–69, 2000; Pandey, A., et al., Characterization of a novel src-like adapter protein that associates with the Eck receptor tyrosine kinase. J Biol Chem, 270: 19201–19204, 1995). Alternatively, EphA2 could alter the expression of important adhesion molecules. Future studies will be needed to identify the molecular targets of EphA2 in malignant cells.

The weakened cell—cell adhesions of EphA2-overexpressing cells are interesting since EphA2 binds a membrane-anchored ligand. EphA2 in non-transformed epithelia was enriched within sites of cell—cell contact, where it interacts with ligand and is tyrosine phosphorylated (Zantek, N. D., et al., 1999). In contrast, EphA2 overexpression destabilizes cell—cell contacts, causes EphA2 to become diffusely distributed and prevents ligand-mediated tyrosine phosphorylation of EphA2. Similarly, the EphA2 in clinical specimens of breast cancer is diffusely distributed and is not tyrosine phosphorylated, which suggests that these regulatory mechanisms are relevant in vivo.

EphA2 stimulation by an artificial ligand reverses the malignant behavior of EphA2-transformed cells. EphrinA1-

$F_c$ also blocks the growth and migration of malignant breast and prostate cancer cells (Zantek, N. D., et al., 1999; Miao, H., et al., 2000). The molecular basis of these inhibitory effects remains largely unknown, although tyrosine phosphorylation of EphA2 facilitates interactions with PI 3-kinase, SHP-2 and a Src-like adapter protein (SLAP), which is intriguing since each protein has been independently found to regulate cell growth or development (Miao, H., et al., 2000; Pandey, A., et al., 1995). Overexpressed receptor tyrosine kinases can facilitate new and efficacious modalities for targeted intervention against cancer cells (Weiner, L. M. Monoclonal antibody therapy of cancer. Seminars Oncol, 26: 43–51, 1999). A recent success arose from antibody targeting of HER2, a receptor tyrosine kinase that is overexpressed on some breast cancer cells (Weiner, L. M., 1999). Unfortunately, HER2 overexpression is limited to one-third of breast carcinomas and is sporadic on other tumor types, which underscores the need for new targets. Our results suggest that EphA2 might provide a target for intervention against metastatic cancer. At minimum, EphA2 overexpression may identify a larger or different set of tumors than HER2. Strong EphA2 immunoreactivity was detected in 5 of 12 (~40%) breast cancer specimens whereas strong HER2 immunoreactivity was limited to 2 of the 12 samples. These data suggest that strategies that restore or mimic the effects of ligand could negatively regulate tumor cell growth and invasiveness (Zantek, N. D., et al., 1999)( Miao, H., et al., 2000). This latter approach would redirect the function of an overexpressed oncoprotein so that it blocks tumor cell growth and invasiveness.

Example 3

Activation-Dependent Proteolysis of EphA2

Activation of EphA2 with EphrinA I -Fc or monoclonal antibodies induces EphA2 proteolysis. Most EphA2 on metastatic cells (>90%) is degraded within 1–2 hours. The mechanism of this proteolysis involves direct interactions with the Cb1 adapter protein, which directs EphA2 to be degraded by proteosomal or lysosomal enzymes. These findings have important implications for understanding causes of EphA2 overexpression in cancer cells (e.g., decreased ligand binding increases protein stability) as a target for cancer therapy.

Example 4

Design of EPhA2 Monoclonal Antibodies

New EphA2 antibodies were synthesized and screened using innovative approaches to optimize targeting of metastatic cells while minimizing toxicities to benign cells. This was accomplished by exploiting epitopes on metastatic cells that are occluded in benign cells by endogenous ligand (Zantek et al., 1999). Biological properties were targeted that are unique to metastatic cells (e.g., anchorage-independent growth, invasion). To accomplish these goals, RIMMS (see above) was combined with DNA-based immunizations delivered via particle bombardment (biolistics). A fusion of the extracellular domain of EphA2 linked to immunoglobulin (EphA2-Fj was used as the immunogen. The procedures described in K. E. Kilpatrick et al, Hybridoma 17, 569 (1998), which is incorporated herein by reference in its entirety for the fusion procedure were utilized, with the following modifications. One SJL female mouse was immunized with 2 overlaying shots (1.25 μg/shot) of EphA2-$F_c$ DNA-coated gold particles into the thoracic region on days 0, 5, 7 and 9 (to total 10 μg DNA), using an Accell gene gun to introduce antigen into epidermal dendritic cells, which secreted and presented the expressed antigen to regional lymph nodes. On day 12, the axillary and brachial lymph nodes were harvested and somatically fused with P3XBcl-2-13 murine myeloma cells. Cells were plated out in hybridoma media for 2 hours before the addition of 2X HAT. The soluble product protein was secreted at high levels. A pool (~300) of new EphA2 antibodies was isolated.

Analyses revealed extraordinary potential for tumor targeting with the new antibodies. Antibodies have been identified that bind the surface of target-positive (MDA-MB-23 1) but not target-deficient (BT474) breast cancer cells and their specificity for EphA2 has been confirmed by immunoprecipitation and Western blot analyses. Screenings for antibody-mediated activation of EphA2 on metastatic cells have been performed and at least two clones, B10 and B13 (also known as B 10.38 and B 13.46), identified as antibodies that activate EphA2 and EphrinA1-$F_c$, as well as a control (B8.91). Importantly, B13-mediated activation of EphA2 blocks the invasiveness of metastatic cells (MDA-MB-231 and PC-3) in Matrigel and, instead, induces a differentiated phenotype (e.g., pseudoacinar formation in Matrigel). B10 and B13 antibodies also block the malignant growth of metastatic cells. For example, a single treatment of MDA-MB-231 or PC-3 cells with B 13 reduces soft agar colonization by at least 70%. Notably, the anchorage-dependent growth of these cells is not inhibited by B 13 suggesting that we have achieved our goal of targeting anchorage-independent growth mechanisms. Importantly, these antibodies do not block the growth or survival of target-deficient tumor cells (BT474) or non-transformed epithelial cells (e.g., MCF-10A, where EphA2 binds ligand). Indeed, B 13-treated MCF-10A cells retain the capacity to grow and form acini when cultured in Matrigel. Finally, data suggest that EphA2 antibody treatment blocks tumor growth in vivo. A single dose of B 13 antibody reduced the size of tumors formed by EphA2-transformed MCF-10A cells by greater than 60%.

Example 5

E-cadherin Regulates the Function of the EphA2 Tyrosine

Cancer cells generally have weak cell—cell adhesions. Studies were performed to demonstrate that unstable cell—cell adhesions prevent EphA2 from interacting with its cell-attached ligands. In particular, the E-cadherin stabilized cell—cell adhesions and allowed EphA2 to bind its ligands. These findings suggest a mechanism whereby E-cadherin functions as a tumor suppressor protein in breast epithelial cells. EphA2 antibodies and an artificial ligand (EphrinA 1-$F_c$) were used to activate EphA2 on metastatic cells. The data showed that EphA2 activation blocks ECM adhesion and DNA synthesis.

Example 6

Activation of EphA2 Kinase Suppression of Integrin Function and Inducement of Focal Adhesion-kinase Dephosphorylation Ligandmediated tyrosine phosphorylation of EphA2 blocked ECM adhesion and migration in PC3 cancer cells. This phenotype arose because ligand-mediated tyrosine phosphorylation of EphA2 facilitated interactions with the SHP-2 tyrosine phosphatase and thereby directed SHP-2 to dephosphorylate the FAK tyrosine kinase.

Example 7

Antibody Targeting of the EphA2 Receptor Tyrosine Kinase on Malignant Carcinomas The most potent antibody inhibitors of tumor cell growth degrade EphA2 and decreased EphA2 expression is sufficient to inhibit malignant behavior. New procedures were used to generate novel monoclonal antibodies against EphA2. Certain characteristics of tumor cell behavior can be exploited to selectively inhibit tumor cells while minimizing toxicities to normal cells.

Tumor cells were targeted using monoclonal antibodies that specifically bind the extracellular domain of EphA2. These new antibodies were necessary because artificial ligands retain the potential to cross-react with other EphA-family kinases (Gale, N. W., Holland, S. J., Valenzuela, D. M., et al. Neuron 17, 9–19 (1996); Pasquale, E. B. Current Opinion in Cell Biology 9, 608–615 (1997)) and because existing EphA2 antibodies either recognize intracellular epitopes or fail to mimic the actions of ligand (Zantek, N. D., Azimi, M., Fedor-Chaiken, M., Wang, B., Brackenbury, R. & Kinch, M. S. Cell Growth & Differentiation 10, 629–638 (1999).) Finally, whereas the biological actions of with artificial ligands are quite transient, generally lasting less than one hour, the biological actions of these new EphA2 antibodies are long-lived, which likely reflects the increased stability of monoclonal antibodies.

One interesting outcome of this study is that EphA2 antibodies selectively inhibit the growth of malignant cells but do not impair the behavior of non-transformed epithelial cells, even those cells that express EphA. These features likely result in part from the differential ligand binding of EphA2 in normal and malignant cells. Since the EphA2 in non-transformed cells is already attached to its ligands, then it is likely that the monoclonal antibodies are sterically occluded from interacting with EphA2. Another possibility is that even if the antibodies were to stimulate the EphA2 on non-transformed epithelial cells, they would convey signals that are normally provided by endogenous ligands. Finally, the gross overexpression of EphA2 on malignant cells might exaggerate the biochemical and biological outcomes of antibody-based stimulation of EphA2 and thereby render tumor cells more susceptible to antibody treatment.

Preparation of DNA Bullets

Qiagen purified DNA encoding the ecdEphA2/Fc chimeric fusion protein was calcium chloride precipitated onto gold particles (Kilpatrick K E et al. Gene gun delivered DNA-based immunizations mediate rapid production of murine monoclonal antibodies to the Flt-3 receptor. Hybridoma 1998;17:569–576). Each cartridge for ecdEphA2/Fc was prepared to contain a total of 1.25 g of DNA coated onto 0.5 mg of gold particles. Bullets were stored at 4° C. in the dark in the presence of desiccant.

DNA-based Immunizations

One week old female SJL mouse (Jackson Laboratories, Bar Harbor, Me.) was anesthetized with isoflurane for removal of fur and for immunization time points as reported (Kilpatrick K E et al. Gene gun delivered DNA-based immunizations mediate rapid production of murine monoclonal antibodies to the Flt-3 receptor. Hybridoma 1998;17:569–576). The helium-driven PowderJect gene gun, regulated under 375 pounds per square inch pressure was used. DNA-coated gold particles were propelled into the epidermal tissue of the thoracic site. Two ecdEphA2/Fc cartridges containing a total of 2.5 g were delivered in overlaying shots to the thoracic site on days 0, 5, 7, and 9 to total 10 g of ecdEphA2 plasmid.

Peg-induced Somatic Fusion of Immune PL

On day 12 lymphocytes harvested bilaterally from the axillary and brachial lymph nodes of the immunized mouse were harvested, then lymphocytes were fused with P3XBcl-2-13 cells at a ratio of 2.5:1 using a previously reported protocol. (Kilpatrick K E et al. Gene gun delivered DNA-based immunizations mediate rapid production of murine monoclonal antibodies to the Flt-3 receptor. Hybridoma (1998) 17:569–576; Kilpatrick K E et al. High Affinity Morioclonal antibodies generated in less than 30 days using 5 g of DNA. Hybridoma (2000) 19:297–302).

Fluorescent Cell ELISA (Fluorelisa)

Detection of cell surface binding of the EphA2 receptor by anti-EphA2 antibodies was performed using modifications to a previously reported assay (Kilpatrick K E et al. Gene gun delivered DNA-based immunizations mediate rapid production of murine monoclonal antibodies to the Flt-3 receptor. Hybridoma (1998) 17:569–576). 96 well flat-bottom tissue culture treated plates (Costar Cat No. 3595, Cambridge, Mass.) were treated with 100 1 per well of Poly-L-Lysine Hydrobromide (Sigma cat. P6282) diluted to 10 g/ml in 0.1M sodium phosphate, pH 8.0 for 1 hr at room temperature (rt). Poly-L-Lysine was flicked out of the wells and 100 1 of a cell suspension of MDA-MB-231 (positive for EphA2) or MCF10A cells (negative controls) at a concentration of $3 \times 10^4$ cells per well in culturing media was added to respective wells. After the plates were incubated overnight at 37oC, 5% CO2, the culture media was gently flicked from the plates. 100 1 of supernatants from hybridomas or monoclonal cell lines were added to the plates and incubated at room rt for 1 hr. Plates were washed 3 times with 200 1/well of 1X Dulbecco's Phosphate Buffered Saline, pH 7.1 (GIBCOBRL cat. 14200-075). 50 1 of goat anti-mouse Alexa Fluor 488 (Molecular Probes, Eugene, Oreg.), diluted to 2 g/ml in PBS containing 2% FCS was added for 30 min at room temperature (plates were incubated in the dark during this time). Plates were washed as detailed above, then 50 1 PBS containing 2% FCS was added to each well. Wells were immediately observed by fluorescence microscopy using an inverted fluorescence microscope (Model DM-IRB, Leica, Deerfield, Ill.).

Isolation and Characterization of EphA2 Antibodies

To generate monoclonal antibodies against epitopes on the extracellular domain of EphA2, gene gun-based immunizations were combined with the RIMMS (repetitive immunization, multiple sites) immunization protocol as described. Briefly, using an Accell gene gun, an SJL mouse was repetitively immunized with a cDNA that encoded for a fusion protein of the EphA2 extracellular domain that had been linked to immunoglobulin (EphA2-Fc). By transfecting epidermal cells in vivo, the EphA2-Fc protein was properly folded, modified and secreted so that it more closely resembled its physiological counterpart than could have been achieved using purified peptides. The mice were immunized using an abbreviated immunization schedule (12 days) to minimize immunodominance 14. Responding B lymphocytes were then isolated from primary lymph nodes to ensure that class switching and affinity maturation had taken place and to maximize the diversity of antigen recognition. These B lymphocytes were then fused with a myeloma (P3XBcl-2-13) that had been engineered to overexpress Bcl-2 in an effort to minimize apoptosis during the fusion and subcloning procedures. (Kilpatrick, K. E et al. Hybridoma 17, 569–576 (1998)). The resulting hybridoma cells were divided into 48 different bulk cultures immediately following PEG-induced fusion.

As a preliminary screen for EphA2-immunoreactivity, supernatants from bulk culture hybridomas were collected and screened for their ability to stain viable EphA2-overexpressing tumor cells as measured using a fluorescence-based ELISA protocol (FluorELISA). Since the immunization strategy was intended to generate antibodies that recognize native EphA2 on tumor cells, this particular screening approach was preferable over western blot analyses, which might have biased against antibodies with conformation-restricted epitopes. FluorELISA strategy identified 44 bulk populations that stained EphA2-overexpressing tumor cells (MDA-MB-231, PC-3) but not EphA2-deficient cells (BT474). The immunoreactivity was confirmed using fluorescence microscopy, which revealed a pattern of diffuse membrane staining that was consistent with previous studies of EphA2 subcellular localization. (Zantek, N. D. et al. Cell Growth & Differentiation 10, 629–638 (1999); Zelinski, D. P. et al. Cancer Res 61, 2301–2306 (2001)). Based on strong immunoreactivity, hybridoma bulk cultures were selected for subcloning by flow cytometry and FluorELISA was repeated on supernatants collected from subcloned hybridomas.

The specificity of hybridoma subclones for EphA2 was confirmed using multiple analyses. First, cell lysates were collected from EphA2-overexpressing (MDA-MB-231, PC-3) and EphA2-deficient (LNCaP, BT474) cell lines and immunoprecipitated with each candidate antibody. The resulting material was then resolved and subjected to western blot analyses with known EphA2 antibodies (D7, EK166B). The inverse experiment confirmed EphA2 specificity but revealed that some antibodies (B8, B10) could be used for western blotting whereas others (B13) recognized epitopes that were ablated by denaturing conditions. Finally, each candidate antibody was isotyped and all were found to be of the IgG1 subclass (Table V). Based on these analyses, the three most immunoreactive EphA2-specific subclones (B8, B10 and B13) were selected for further analysis.

TABLE V

Overview of EphA2 Antibodies

| Ab | Isotype | WB | IP | IF | EphA2 Activation | EphA2 Degradation | Soft Agar Inhibition | Channel Inhibition |
|---|---|---|---|---|---|---|---|---|
| B8 | IgG$_1$ | + | + | + | − | − | − | − |
| B10 | IgG$_1$ | + | + | + | + | + | + | + |
| B13 | IgG$_1$ | − | + | + | ++ | ++ | ++ | ++ |
| B2D6 | IgG$_{2b}$ | − | + | + | − | − | − | − |
| D7 | IgG$_1$ | + | + | + | − | − | − | − |
| EA1F$_c$ | na | − | + | + | + | + | +/− | − |

Table V. Shown is an overview of the EphA2 antibodies used in this study. The antibodies were evaluated for their technical applications as measured using western blot analyses (WB), immunoprecipitation (IP) and immunofluorescence staining (IF) and for their ability to inhibit tumor (MDA-MB-231, PC-3) cell growth in soft agar or channel formation on Matrigel. Note that the B2D6 and D7 antibodies served as negative controls for EphA2 activation. Ea1Fc represents the artifical ligand for EphA2 that has been used in previous studies to activate EphA2.

Selective Inhibition of Malignant Cell Growth

The EphA2 antibodies were first evaluated for their potential to inhibit the growth and invasiveness of aggressive breast and prostate cancer cells. Based on our recent demonstration that EphA2 overexpression facilitates anchorage-independent cell growth in a foreign microenvironment, treatment of EphA2-overexpressing cells with specific antibodies was tested to see whether such treatment could prevent tumor cell colonization of soft agar. MDA-MB-231 cells were suspended in soft agar in the presence of absence of 10 g /mL purified antibody for 0–21 days. Microscopic evaluation of colony formation revealed that B10 or B13 antibodies inhibited at least 60% of soft agar colony formation as compared to matched controls. Notably, B8 antibodies did not impair soft agar colonization. Identical results were obtained following treatment of PC-3 cells with B8, B10 and B13 and, unless noted otherwise, all subsequent results were reproduced using both MDA-MB-231 and PC-3 cells. As a control, EphA2 antibodies did not block the ability of EphA2-deficient cells (LNCaP, BT474) to colonize soft agar. In addition, isotype matched antibodies that do not bind extracellular epitopes on EphA2 (e.g., D7, anti-paxillin) also did not alter colony formation in soft agar. The EphA2 antibodies selectively inhibited tumor cell growth in a foreign microenvironment. To test this, $1 \times 10^4$ non-transformed (MCF-10A) or malignant (MDA-MB-231) cells were cultured in monolayer assays and cell growth was measured at daily intervals. Notably, none of the EphA2 antibodies altered the log-phase growth of MDA-MB-231. However, upon reaching confluence (day 7), there was a reproducible decrease in the growth of samples that had been treated with B13 antibodies as compared to matched controls. Thus, the growth-inhibitory effects of B13 antibodies were most effective as the tumor cells switched from anchorage-dependent to anchorage-independent growth.

To test further whether these effects were specific for malignant cell growth, identical studies were performed using non-transformed MCF-10A mammary epithelial cells. Despite the fact that MCF-10A cells expressed EphA2, none of the antibodies decreased their growth at any dose or time point. Similarly, none of the antibodies altered the growth of target-deficient tumor cells (e.g., BT474), thus confirming their specificity for EphA2. Taken together, these analyses identify a population of EphA2 antibodies, represented by B10 and B13, that selectively impair the malignant growth of tumor cells.

Over the short-term, antibody stimulation triggers EphA2 autophosphorylation and thereby triggers a variety of intracellular signals that might be expected to enhance tumor cell growth and invasiveness. Angrist, M. et al. Genomics 30, 623–625 (1995); Miao, H., Burnett, E., Kinch, M. S., Simon, E. & Wang, B. Nature Cell Biol 2, 62–69 (2000); Pandey, A., Lazar, D. F., Saltiel, A. R. & Dixit, V. M. Journal of Biological Chemistry 269, 30154–30157 (1994).) The duration of EphA2 signaling in response to antibody binding is approximately 10–30 minutes. Over the longer term (beyond 60 minutes), the primary consequence of antibody binding is EphA2 degradation. Similarly, ligand-mediated stimulation induces EphA2 degradation. Thus, EphA2 antibodies like B13 may function primarily by removing a powerful oncoprotein from malignant cells. A similar mechanism has been proposed to explain the biological actions of Herceptin, which stimulates autophosphorylation of the HER2 oncoprotein. (Sliwkowski, M. X. et al. Seminars in Oncology 26, 60–70 (1999).)

An alternative but not mutually exclusive possibility is that signals emanating from antibody-activated EphA2 actively inhibits, rather than enhances, tumor cell growth. Consistent with this hypothesis, ligand-mediated activation of EphA2 has been shown to inhibit tumor cell binding to the underlying extracellular matrix. Miao, H., Burnett, E., Kinch, M. S., Simon, E. & Wang, B. Nature Cell Biol 2, 62–69 (2000); Zantek, N. D. et al. Cell Growth & Differentiation 10, 629–638 (1999). It is generally understood that cell-ECM interactions initiate signals that are necessary for cell growth, survival, migration, and invasion. (Ruoslahti, E. Advances in Cancer Research 76, 1–20 (1999b); Frisch, S.

M. & Ruoslahti, E. Current Opinion in Cell Biology 9, 701–706 (1997).) Since activated EphA2 destabilizes ECM contacts at focal adhesions, it is possible that the resulting decrease in ECM-mediated signaling also contributes to the growth-inhibitory actions of EphA2 antibodies.

Inhibition of Channel Formation in 3dRBM

The differences in assays that measure soft agar versus monolayer growth might indicate that EphA2 antibodies exert their most profound effects when analyzed in three-dimensional assays. Thus, studies were performed to assess whether EphA2 antibodies would alter the behavior of benign and malignant cells in three-dimensional, reconstituted basement membranes (3dRBM). To analyze three-dimensional cell behavior, monolayer cultures of MCF-10A or MDA-MB-231 cells were incubated atop or within Matrigel. Non-transformed MCF-10A epithelial cells organized into acinus-like spheres on Matrigel, which was consistent with their differentiated phenotype. (Zelinski, D. P. et al. Cancer Res 61, 2301–2306 (2001).) None of the EphA2 antibodies (B8, B10 or B13) hindered the ability of MCF-10A cells to become organized into differentiated spheres and no indications of antibody-induced toxicity to the non-transformed cells were detected. In contrast, aggressive MDA-MB-231 tumor cells quickly assembled into channels that invaded all throughout the Matrigel and this behavior was highly sensitive to EphA2 antibodies. Treatment of MDA-MB-231 cells with B10 or B13 (but not B8) antibodies prevented channel formation. Instead the tumor cells organized into spherical structures that resembled the behavior of differentiated cells, albeit the spheres were 2–5 times larger than the structures formed by MCF-10A. This dramatic change in behavior was reproduced using other EphA2-overexpressing cells (e.g., PC-3) and it is notable that PC-3 cells also demonstrated gross evidence of cell death in the presence of B10 or B13 antibodies. These analyses confirmed that certain EphA2 antibodies selectively inhibit the malignant behavior of aggressive carcinoma cells and that three-dimensional assays accentuate the biological responses of tumor cells to these antibodies.

Activation-Dependent Degradation of EphA2

The mechanisms by which EphA2 antibodies selectively inhibit the malignant behavior of metastatic cells were investigated. These studies were assisted by consistent evidence that B10 and B13 antibodies inhibited malignant behavior whereas B8 antibodies did not. The lack of B8 biological activity did not reflect a failure to bind EphA2 on tumor cells since B8 interacted as well as B10 or B13 with the EphA2 on tumor cells as measured using flow cytometry, FluorELISA, immunofluorescence microscopy, and immunoprecipitation. To begin examining the biochemical consequences of antibody treatment, MDA-MB-231 or PC-3 cells were incubated with EphA2 antibodies at 37° C. The phosphotyrosine content of immunoprecipitated EphA2 was measured by western blot analysis with specific antibodies (a cocktail of PY20 and 4G10), which revealed dramatic differences in how each antibody stimulated EphA2 autophosphorylation. B10 or B13 antibodies induced dramatic increases in the phosphotyrosine content of EphA2 and in a dose-dependent manner. The autophosphorylation of EphA2 was rapid, detected within 2–5 minutes and B13 antibodies reproducibly induced EphA2 autophosphorylation more efficiently than B10 antibodies. In contrast, B8 antibodies did not induce receptor autophosphorylation at any dose or time point. Thus, the growth-inhibitory actions of EphA2 antibodies related to their abilities to induce receptor autophosphorylation.

Whether and how EphA2 autophosphorylation related to antibody inhibition of tumor cell growth was further investigated. The phosphotyrosine content of EphA2 decreased approximately one hour after antibody treatment and remained at low levels thereafter. By stripping and re-probing the membranes with EphA2-specific antibodies, decreased phosphotyrosine content was determined to represent decreased EphA2 protein levels. The protein levels of EphA2 were evaluated over time, revealing that EphA2 levels were suppressed for at least 24–48 hours after the treatment with either B10 or B13 antibodies. In contrast, B8 treatment did not alter the levels of EphA2, which was consistent with the inability of B8 to trigger EphA2 autophosphorylation. Identical results were obtained using whole cell lysates and immunoprecipitated material and by probing the membranes with different EphA2 antibodies (D7, EK166B, polyclonal sera, and B8), indicating that that decreased EphA2 protein levels did not represent the loss of immunoreactivity by any particular EphA2 antibody. Notably, antibody-induced degradation was detected when the tumor cells were cultured in either two-dimensional or three-dimensional assay systems and indeed, the EphA2 in anchorage-independent cultures seemed to be more sensitive to degradation than the EphA2 in monolayer culture. Thus, selective inhibition of tumor cell growth and invasiveness relates to the ability of antibodies to induce EphA2 activation and degradation.

Decreased EphA2 Levels Are Sufficient to Block Tumor Cell Growth

Recent studies have shown that ligand-mediated autophosphorylation transduces signals downstream of EphA2. (Easty, D. J et al. Cancer Research 55, 2528–2532 (1995); Miao, H. et al. Nature Cell Biol 2, 62–69 (2000); Pandey, A. et al., Journal of Biological Chemistry 269, 30154–30157 (1994); Pandey, A. et al. Science 268, 567–569 (1995).) Since B10 and B13 antibodies trigger both autophosphorylation and EphA2 degradation, it was unclear whether either or both responses were responsible for decreased tumor cell growth in response to Eph2 antibodies. These possibilities were distinguished by developing an antisense oligonucleotide-based strategy that decreased EphA2 expression in tumor cells without inducing EphA2 autophosphorylation. Monolayers of MDA-MB-231 cells were treated with 300 ng/mL of an antisense oligonucleotide that was specific for human EphA2. As a matched control, parallel samples were treated with an inverted antisense oligonucleotide. Western blot analyses confirmed that antisense oligonucleotides decreased EphA2 expression in MDA-MB-231 cells and then analyzed was whether decreased EphA2 levels would affect soft agar colonization. Indeed, EphA2 antisense oligonucleotides decreased the ability of MDA-MB-231 cells to colonize soft agar by at least 60% as compared to matched controls. Thus, consistent results with EphA2 antibodies and antisense oligonucleotides suggest that EphA2 antibodies inhibit malignant cell growth by reducing EphA2 levels on tumor cells.

The complete disclosures of all patents, patent applications including provisional patent applications, and publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

Throughout this application, various publications are referenced. The disclosures of these publications in their entireties are hereby incorporated by reference into this application in order to describe more fully the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A monoclonal antibody produced by hybridoma B13 (ATCC Accession Number PTA-3711).

2. An antibody reagent kit comprising containers of the monoclonal antibody or antigen-binding fragment thereof of claim 1 and one or more reagents for detecting binding of the antibody or antigen-binding fragment thereof to the EphA2 receptor molecule.

3. An antigen-binding fragment of the antibody of claim 1, wherein the antigen-binding fragment binds to an EphA2 receptor molecule.

4. The antibody fragment of claim 3, wherein the fragment competes for receptor binding with a natural ligand of the EphA2 receptor molecule.

5. The antibody fragment of claim 4, wherein the natural ligand is an ephrin.

6. A monoclonal antibody obtained by humanizing the monoclonal antibody produced by hybridoma B13 (ATCC Accession Number PTA-3711), wherein said humanized antibody binds to an EphA2 receptor molecule.

7. The antibody of claim 6 wherein the antibody competes for receptor binding with a natural ligand of the EphA$^2$ receptor molecule.

8. The antibody of claim 7, wherein the natural ligand is an ephrin.

9. An antigen-binding fragment of the antibody of claim 6, wherein the antigen-binding fragment binds to an EphA2 receptor molecule.

10. The antibody fragment of claim 9 wherein the fragment competes for receptor binding with a natural ligand of the EphA2 receptor molecule.

11. The antibody fragment of claim 9, wherein the natural ligand is an ephrin.

12. An human antibody that binds to the same epitope of an EphA2 receptor molecule as the monoclonal antibody produced by hybridoma B13 (ATCC Accession Number PTA-3711).

13. An antigen-binding fragment of the antibody of claim 12 wherein the antigen-binding fragment binds to an EphA2 receptor.

14. A cell of hybridoma B13 (ATCC Accession Number PTA-3711).

15. A humanized antibody that binds to an EphA2 receptor molecule, wherein the antibody binds the binds the same epitope as the monoclonal antibody produced by hybridoma B13 (ATCC Accession Number PAT-3711).

16. The human antibody of claim 12 wherein the antibody is produced by a germ-line mutant animal.

17. The human antibody of claim 12, wherein the antibody is produced by a phage display library.

18. An isolated antibody that binds to an EphA2 receptor, wherein the antibody binds the same epitope as a monoclonal antibody produced by hybridoma B13 (ATCC Accession Number PTA-3711).

19. The antibody of claim 18, wherein the antibody is a mammalian antibody.

20. The antibody of claim 19, wherein the antibody is produced by a germ-line mutant animal.

21. The antibody of claim 20, wherein the antibody is a human antibody produced by a phage display library.

* * * * *

UNITED STATES PATENT AND TRADEMARK OFFICE
CERTIFICATE OF CORRECTION

PATENT NO. : 7,101,976 B1 Page 1 of 1
APPLICATION NO. : 09/952560
DATED : September 5, 2006
INVENTOR(S) : Kilpatrick et al.

It is certified that error appears in the above-identified patent and that said Letters Patent is hereby corrected as shown below:

Col. 1 after related patent data please insert
--GOVERNMENT INTEREST
This work was supported by Army Breast Cancer Research Grant No. DAMD-98-1-8146 awarded by the U.S. Department of Defense; National Institutes of Health Grant No. AR 44713; and U.S. Army Medical Research and Material Command Grant No. 17-98-1-8146. Thus, the U.S. Government has certain rights in the presently disclosed subject matter.--

Signed and Sealed this

Twenty-third Day of January, 2007

JON W. DUDAS
*Director of the United States Patent and Trademark Office*